(12) United States Patent
Miyamoto

(10) Patent No.: US 9,360,456 B2
(45) Date of Patent: Jun. 7, 2016

(54) DETECTING APPARATUS, POWER RECEIVING APPARATUS, POWER TRANSMITTING APPARATUS, AND CONTACTLESS POWER SUPPLY SYSTEM

(71) Applicant: Sony Corporation, Tokyo (JP)

(72) Inventor: Takashi Miyamoto, Chiba (JP)

(73) Assignee: Sony Corporation, Tokyo (JP)

( * ) Notice: Subject to any disclaimer, the term of this patent is extended or adjusted under 35 U.S.C. 154(b) by 553 days.

(21) Appl. No.: 13/789,108

(22) Filed: Mar. 7, 2013

(65) Prior Publication Data

US 2013/0241300 A1    Sep. 19, 2013

(30) Foreign Application Priority Data

Mar. 14, 2012    (JP) ................... 2012-057538

(51) Int. Cl.
*G01N 27/72* (2006.01)
*H01F 38/14* (2006.01)
*H01F 5/00* (2006.01)

(52) U.S. Cl.
CPC .............. *G01N 27/72* (2013.01); *H01F 5/003* (2013.01); *H01F 38/14* (2013.01)

(58) Field of Classification Search
CPC ........... H02J 5/005; H02J 7/025; H02J 17/00; H01F 38/14; B60L 11/182; G01N 27/00; G01N 27/72; H04B 5/0037; H04B 5/0087
USPC ........................................................ 307/104
See application file for complete search history.

(56) References Cited

U.S. PATENT DOCUMENTS

| | | | |
|---|---|---|---|
| 8,957,549 B2* | 2/2015 | Kesler | 307/104 |
| 9,106,203 B2* | 8/2015 | Kesler | H03H 7/40 |
| 2006/0049928 A1* | 3/2006 | Ening | G06K 7/10336 340/448 |
| 2007/0120636 A1* | 5/2007 | Chen | H01F 3/14 336/178 |
| 2007/0145830 A1* | 6/2007 | Lee | H02J 5/005 307/135 |
| 2008/0024255 A1* | 1/2008 | Sano | H01F 27/255 335/297 |
| 2012/0256494 A1* | 10/2012 | Kesler | H03H 7/40 307/104 |
| 2013/0069441 A1* | 3/2013 | Verghese | G01R 33/10 307/104 |
| 2013/0093257 A1* | 4/2013 | Goto | H02J 5/005 307/104 |
| 2013/0207763 A1* | 8/2013 | Wagoner | H01F 27/22 336/60 |

FOREIGN PATENT DOCUMENTS

| | | |
|---|---|---|
| JP | 2001-275280 | 10/2001 |
| JP | 2008-206231 | 9/2008 |

* cited by examiner

*Primary Examiner* — Thienvu Tran
*Assistant Examiner* — Brian K Baxter
(74) *Attorney, Agent, or Firm* — Chip Law Group

(57) ABSTRACT

There is provided a detecting apparatus including one or a plurality of magnetic coupling elements that include a plurality of coils, a positioning unit disposed near at least one coil from among the plurality of coils included in the one or plurality of magnetic coupling elements, and a detector that measures an electrical parameter related to the one or plurality of magnetic coupling elements or to a circuit that at least includes the one or plurality of magnetic coupling elements, and determines from a change in the electrical parameter whether a foreign matter capable of generating heat due to magnetic flux is present.

15 Claims, 19 Drawing Sheets

A
FIRST EXAMPLE

B
FIRST EXAMPLE
(INSIDE DIAMETER
OF L2 >
INSIDE DIAMETER
OF L3)

A
SPIRAL SHAPE

B
FIGURE 8 SHAPE

A

B

A

B

DETECTING APPARATUS, POWER RECEIVING APPARATUS, POWER TRANSMITTING APPARATUS, AND CONTACTLESS POWER SUPPLY SYSTEM

CROSS REFERENCES TO RELATED APPLICATIONS

The present application claims priority to Japanese Priority Patent Application JP 2012-057538 filed in the Japan Patent Office on Mar. 14, 2012, the entire content of which is hereby incorporated by reference.

BACKGROUND

The present disclosure relates to a magnetic coupling element that magnetically couples with another magnetic coupling element or foreign matter, and to an apparatus (magnetic coupling apparatus) and system (magnetic coupling system) utilizing such a magnetic coupling element.

More particularly, the present disclosure relates to a detecting apparatus, a power receiving apparatus, a power transmitting apparatus, and a contactless power supply system configured to detect the presence of foreign matter (such as metal, a magnetized body, or magnet) which may generate heat due to magnetic flux between a contactless power supplying apparatus and an electronic device constituting a contactless power supply system.

Recently, increasing attention is being given to power supply systems that supply power (transfer power) to a consumer electronics (CE) device, such as a mobile phone or portable music player, for example, in a contactless manner (referred to as contactless power supply systems or contactless power transfer systems, for example). With such systems, charging is initiated not by inserting (connecting) the connector of an AC adapter or other power supply apparatus into a CE device, but rather by simply placing an electronic device (the secondary device) onto a charging tray (the primary device). In other words, a terminal connection between the electronic device and the charging tray is unnecessary.

Electromagnetic induction is established as a technique for supplying power in a contactless manner as above. Meanwhile, contactless power supply systems using a technique called magnetic resonance which utilizes the resonance phenomenon have been gaining attention recently.

Contactless power supply systems using magnetic resonance are advantageous in that the principle of the resonance phenomenon may be utilized to transfer power between devices separated by greater distances than those of electromagnetic induction. Additionally, there is an advantage in that the transfer efficiency (power supply efficiency) does not fall significantly even if the axis alignment between the power source (transmitter coil) and power recipient (receiver coil) is somewhat poor. However, magnetic resonance-based systems and electromagnetic induction-based systems are alike in that both are contactless power supply systems (magnetic coupling systems) utilizing a power source (transmitter coil; a magnetic coupling element) and a power recipient (receiver coil; a magnetic coupling element).

Meanwhile, one important element in contactless power supply systems is the thermal regulation of foreign matter, such as metals, magnetized bodies, and magnets, which may generate heat due to magnetic flux. If foreign matter becomes interposed in the gap between the transmitter coil and the receiver coil when supplying power in a contactless manner, there is a risk of causing the foreign matter to generate heat due to the magnetic flux passing through that foreign matter. This risk is not limited to electromagnetic induction-based or magnetic resonance-based systems. Such heat generation in foreign matter may lead to currents being produced in a foreign metal due to the magnetic flux passing through the foreign metal (eddy currents, current loops, circular currents), or to hysteresis loss being produced in a foreign magnetized body or foreign magnet due to the magnetic flux passing through the foreign magnetized body or foreign magnet.

A large number of techniques that detect foreign metal by adding a foreign matter detection system to a contactless power supply system have been proposed for such thermal regulation. For example, techniques using an optical sensor or a temperature sensor have been proposed. However, detection methods that use sensors may be costly in the case of a broad power supply range, as with magnetic resonance-based systems. Moreover, use of a temperature sensor, for example, may impose additional design constraints on the transmitting and receiving devices, since the output results from the temperature sensor will depend on its surrounding thermal conductivity.

Thus, there have been proposed techniques that determine the presence of foreign metal by looking at changes in parameters (such as current and voltage) when a foreign metal comes between the transmitter and receiver. With such techniques, it is possible to curtail costs without imposing design or other constraints.

For example, JP 2008-206231A proposes a method of detecting foreign metal according to the modulation rate (information on amplitude and phase changes) during communication between the transmitter and receiver, while JP 2001-275280A proposes a method of detecting foreign metal according to eddy current loss (foreign matter detection according to DC-DC efficiency).

SUMMARY

However, the techniques proposed in JP 2008-206231A and JP 2001-275280A do not take into account the effects of a metal housing at the receiver. Consider the case of charging a typical portable device. It is highly probably that some kind of metal (such as a metal housing or metal components) is used in the portable device, and thus it is difficult to clearly determine whether a change of parameters is due to the effects of the metal housing or components, or due to the presence of foreign metal. To take JP 2001-275280A as an example, it is indeterminate whether eddy current loss occurs because of the metal housing of the portable device, or because foreign metal is present between the transmitter and receiver. In this way, it can hardly be said that the techniques proposed in JP 2008-206231A and JP 2001-275280A are able to accurately detect foreign metal.

Being devised in light of the above circumstances, an embodiment according to the embodiment of the present disclosure detects foreign matter in close proximity to a detector coil (in other words, a magnetic coupling element) without providing an additional sensor, and furthermore improves detection accuracy.

According to an embodiment of the present disclosure, there is provided a detecting apparatus including one or a plurality of magnetic coupling elements that include a plurality of coils, a positioning unit disposed near at least one coil from among the plurality of coils included in the one or plurality of magnetic coupling elements, and a detector that measures an electrical parameter related to the one or plurality of magnetic coupling elements or to a circuit that at least includes the one or plurality of magnetic coupling elements, and determines from a change in the electrical parameter whether a foreign matter that generates heat due to magnetic flux is present.

According to an aspect of the present disclosure, it is possible to reliably affix a magnetic coupling element at a desired position with respect to a contactless power supply coil by disposing positioning units in the vicinity of at least one coil from among multiple coils constituting the magnetic coupling element. Thus, detection accuracy variations among individual foreign matter detecting apparatus is mitigated.

According to at least one aspect of the present disclosure, it is possible, without providing an additional sensor, to detect foreign matter which is in close proximity to a magnetic coupling element and which may generate heat due to magnetic flux, and furthermore greatly improve detection accuracy.

Additional features and advantages are described herein, and will be apparent from the following Detailed Description and the figures.

BRIEF DESCRIPTION OF THE FIGURES

FIG. 6A illustrates an exemplary perspective view configuration and FIG. 6B illustrates an exemplary plan view configuration including positioning units;

FIG. 8A is a diagrammatic cross-section view regarding a spiral-shaped coil and the distribution of magnetic field lines produced from that coil, while FIG. 8B is a diagrammatic cross-section view regarding a figure 8-shaped coil according to an embodiment of the present disclosure and the distribution of magnetic field lines from that coil;

FIG. 14A is a plan view illustrating a first example, and FIG. 14B is a plan view illustrating a second example;

FIG. 16A is a plan view illustrating a first example, and FIG. 16B is a plan view illustrating a second example;

FIGS. 17A, 17B, and 17C are plan views illustrating an example of a receiver coil, an example in which multiple detector coils are disposed on top of the receiver coil, and an example in which some detector coils are disposed in the center of the receiver coil, respectively;

FIGS. 18A, 18B, and 18C are plan views illustrating an example of a receiver coil and foreign metal, an example in which multiple detector coils are disposed on top of the receiver coil, and an example in which multiple detector coils are additionally disposed on top of the multiple detector coils in FIG. 18B, respectively;

FIGS. 19A and 19B are plan views illustrating an example in which multiple detector coils are disposed on top of the receiver coil, and an example in which multiple detector coils are additionally disposed on top of the multiple detector coils in FIG. 19A, respectively;

DETAILED DESCRIPTION

Figure 1:
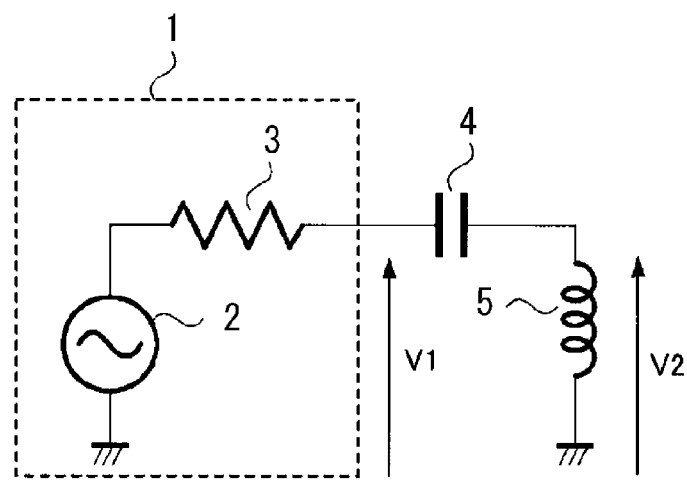
FIG. 1 is a schematic circuit diagram accompanying an explanation of Q factor measurement used as an example of foreign metal detection according to an embodiment of the present disclosure.

Hereinafter, preferred embodiments of the present disclosure will be described in detail with reference to the appended drawings. Note that, in this specification and the appended drawings, structural elements that have substantially the same function and structure are denoted with the same reference numerals, and repeated explanation of these structural elements is omitted.

Hereinafter, the description will proceed in the following order.

1. Introductory explanation
2. First embodiment (positioning units: example of detector coil and receiver coil disposed in same plane)
3. Second embodiment (positioning units: example of detector coil and receiver coil not disposed in same plane)
4. Third embodiment (positioning units: example of positioning receiver coil before detector coil)
5. Fourth embodiment (positioning units: example of adjusting electrical properties)
6. Other 1. Introductory Explanation In the present disclosure, there is proposed a magnetic coupling system that detects foreign matter on the basis of an electrical parameter for a circuit at a transmitter or a receiver when charging a component such as a battery in the receiver (secondary device) with power supplied from the transmitter (primary device). In a magnetic coupling system according to an embodiment of the present disclosure, an electrical parameter is measured for a circuit in a transmitter or a receiver, the circuit at least including one or multiple magnetic coupling elements which magnetically couple with an external element and which are realized with multiple coils. The presence of foreign matter in close proximity to the magnetic coupling element is then determined on the basis of the electrical parameter measurement results.

Hereinafter, a description will be given using, as an example, the case where the above circuit at least including a magnetic coupling element is a resonant circuit, while in addition, the above electrical parameter is the quality factor (Q factor). The Q factor is an index expressing the relationship between energy storage and loss, and is typically used as a factor expressing the sharpness of the resonance peak (in other words, the resonance strength) in a resonant circuit.

Note that although the descriptions of the respective embodiments of the present disclosure in this specification cite the detection of foreign metal as an example, the detection of other foreign matter (such as foreign magnetized bodies and foreign magnets) is also similar.

[Q Factor Measurement Principle]

Hereinafter, the principle of Q factor measurement will be described with reference to the drawings.

FIG. 1 is a schematic circuit diagram accompanying an explanation of Q factor measurement used for foreign metal detection according to an embodiment of the present disclosure.

The circuit illustrated in FIG. 1 is an example of a basic circuit layout (for the case of magnetic coupling) illustrating the principle of Q factor measurement. The circuit is provided with a signal source 1, which includes an alternating current (AC) power source 2 that produces an AC signal (sine wave) and a resistive element 3, as well as a capacitor 4 and a coil 5. The resistive element 3 is an illustration of the internal resistance (output impedance) of the AC power source 2. The capacitor 4 and the coil 5 are connected to the signal source 1 so as to form a series resonant circuit (one example of a resonant circuit). The resonant circuit resonates at a given frequency (the resonant frequency) according to the capacitance value (C value) of the capacitor 4 and the inductance value (L value) of the coil 5.

Although FIG. 1 illustrates a circuit provided with a series resonant circuit realized with a coil 5 and a capacitor 4, various layouts are conceivable for the detailed configuration, insofar as resonant circuit functionality is provided.

If foreign metal, such as a metal fragment, for example, is present near the coil 5, the magnetic field lines will pass through the metal fragment, and eddy currents will be produced in the metal fragment. From the perspective of the coil 5, the metal fragment and the coil 5 are magnetically coupled and it appears as though a resistive load has been attached to the coil 5, changing the Q factor of the coil (resonant circuit). Measuring the Q factor thus leads to detection of foreign metal near the coil 5 (in other words, a magnetically coupled state).

At this point, take V1 to be the voltage across the ends of the coil 5 and the capacitor 4 constituting the series resonant circuit (an example of voltage applied to a resonant circuit), and take V2 to be the voltage across the ends of the coil 5. In this case, the Q factor of the series resonant circuit is expressed as in Eq. 1, where R is the effective resistance value (series resistance value) for the frequency f of the circuit, L is the inductance value, and C is the capacitance value. When V2>>V1, the equation may be approximated as follows.

$$Q = \frac{1}{R}\sqrt{\frac{L}{C}} = \frac{V2 - V1}{V1} \cong \frac{V2}{V1} \quad (1)$$

In the circuit illustrated in FIG. 1, the voltage V2 is obtained by multiplying the voltage V1 by a factor of approximately Q. It is established that the series resistance value R and the inductance value L indicated in Eq. 1 change as metal approaches or due to the effects of eddy currents produced in the metal. For example, if a metal fragment approaches the coil 5, the effective resistance value R increases, and the Q factor drops. In other words, since the Q factor of the resonant circuit and the resonant frequency change greatly due to the effects of metal present in the vicinity of the coil 5, by detecting such change it is possible to detect a metal fragment present near the coil 5. Additionally, such Q factor measurement may be applied to the detection of foreign metal interposed between a transmitter (primary device) and a receiver (secondary device).

By conducting a foreign metal detection process using changes in the Q factor discussed above, it is possible to detect foreign metal with high accuracy for both electromagnetic induction-based systems and magnetic resonance-based systems, and have the user remove the detected foreign metal.

Overview of Technology According to the Embodiment of the Present Disclosure

Meanwhile, another conceivable technique involves using a detector connected to a circuit including a coil (detector coil) that electromagnetically or magnetically couples with an external element to measure the Q factor of the circuit using an AC signal at a different frequency than the frequency of the AC signal flowing through the transmitter coil and the receiver coil.

Also, as another example, a configuration in which the above detector coil used to measure the Q factor is separate from the transmitter coil and the receiver coil is also conceivable.

By using an AC signal at a different frequency than the frequency of the AC signal flowing through the transmitter coil and the receiver coil, AC signals for contactless power supply are separable from AC signals for Q factor measurement, and thus it becomes possible to measure the Q factor while contactless power supply is in operation. In addition, accurate detection of foreign metal or other matter may be conducted even while contactless power supply is in operation.

However, the detector coil may be greatly affected by the magnetic flux (lines of magnetic force; a magnetic field) for contactless power supply in the case of using a typical spiral-shaped coil 5 as the detector coil that electromagnetically or magnetically couples with an external element. As a result, AC signals for Q factor measurement utilized in foreign matter detection may overlap AC signals for contactless power supply, producing unwanted noise due to the contactless power supply. As a result, foreign metal detection accuracy may decrease greatly.

Also, the above detector coil is readily affected by the transmitter coil and receiver coil used for contactless power supply, as well as by elements such as magnetic materials and metal inside the electronic device housing. Given this issue, if a typical spiral-shaped detector coil is packaged in a device such as a contactless power supply apparatus (hereinafter simply designated "power supply apparatus") or electronic device, the Q factor of the detector coil, which is used as the basis value for determining the presence of foreign metal, may decrease greatly.

Furthermore, foreign metal detection accuracy may change greatly depending on the configuration of the power source (transmitter) and power recipient (receiver) in the contactless power supply system.

In this way, it has been difficult to obtain exact information for foreign matter detection, and the foreign matter detection accuracy has not improved. Accordingly, the inventors have researched a magnetic coupling element that improves foreign matter detection accuracy by obtaining more exact information for foreign matter detection. The inventors then developed one or multiple magnetic coupling elements shaped like multiple coils electrically connected together, in which the magnetic flux produced from at least one or more of these multiple coils and the magnetic flux produced from the remaining of these multiple coils have approximately opposing orientations. Using one or multiple such magnetic coupling elements demonstrated significant improvement in foreign matter detection accuracy.

However, the relative placement of each of the multiple coils constituting the one or multiple magnetic coupling elements becomes extremely important. Also, in the case of using a magnetic coupling element that differs from a contactless power supply coil (such as a detector coil, for example), the relative placement of the contactless power supply coil and the one or multiple magnetic coupling elements also becomes extremely important. In other words, since the Q factor of a magnetic coupling element changes in the case where these relative placements change due to some reason, the foreign matter detection accuracy also changes.

Meanwhile, one conceivable foreign matter detection technique involves detecting whether or not foreign matter is present on the basis of the Q factor of an LC resonator (resonant circuit) that at least includes a magnetic coupling element, or of the magnetic coupling element itself, or on the basis of the numerical value of another electrical parameter that changes in relation to the Q factor, for example. When considering foreign matter detection using such a technique, it is desirable for the magnetic coupling element to have a high Q factor, in order to improve foreign matter detection accuracy.

The disclosure described hereinafter takes the above points into account, and embodiments thereof are proposed as a new technology that improves the Q factor of a magnetic coupling element.

1. First Embodiment

Exemplary Overall Configuration of Contactless Power Supply System

Figure 2:
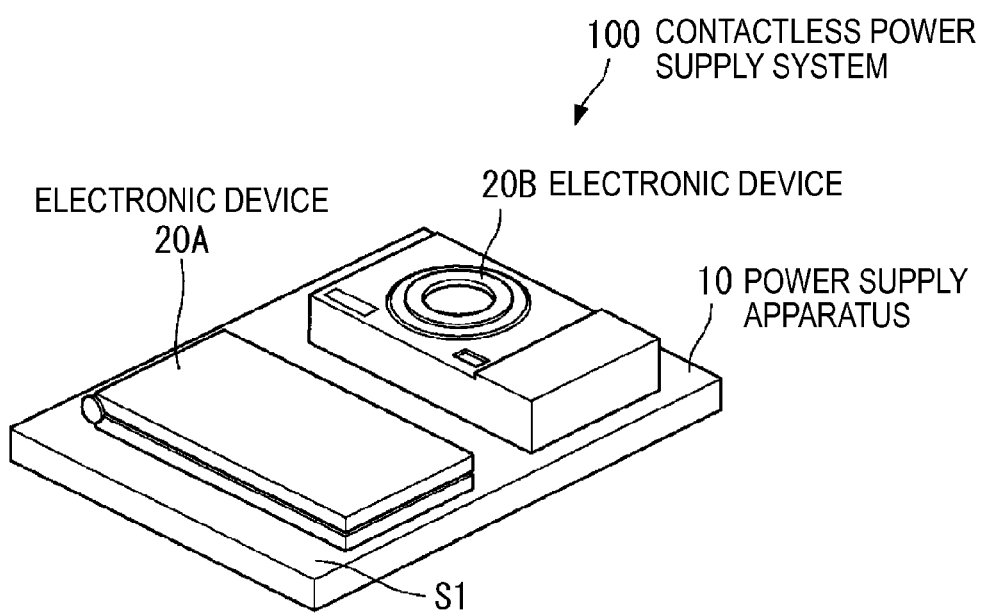
FIG. 2 is a diagrammatic exterior illustration of a contactless power supply system according to the first embodiment of the present disclosure.
Figure 3:
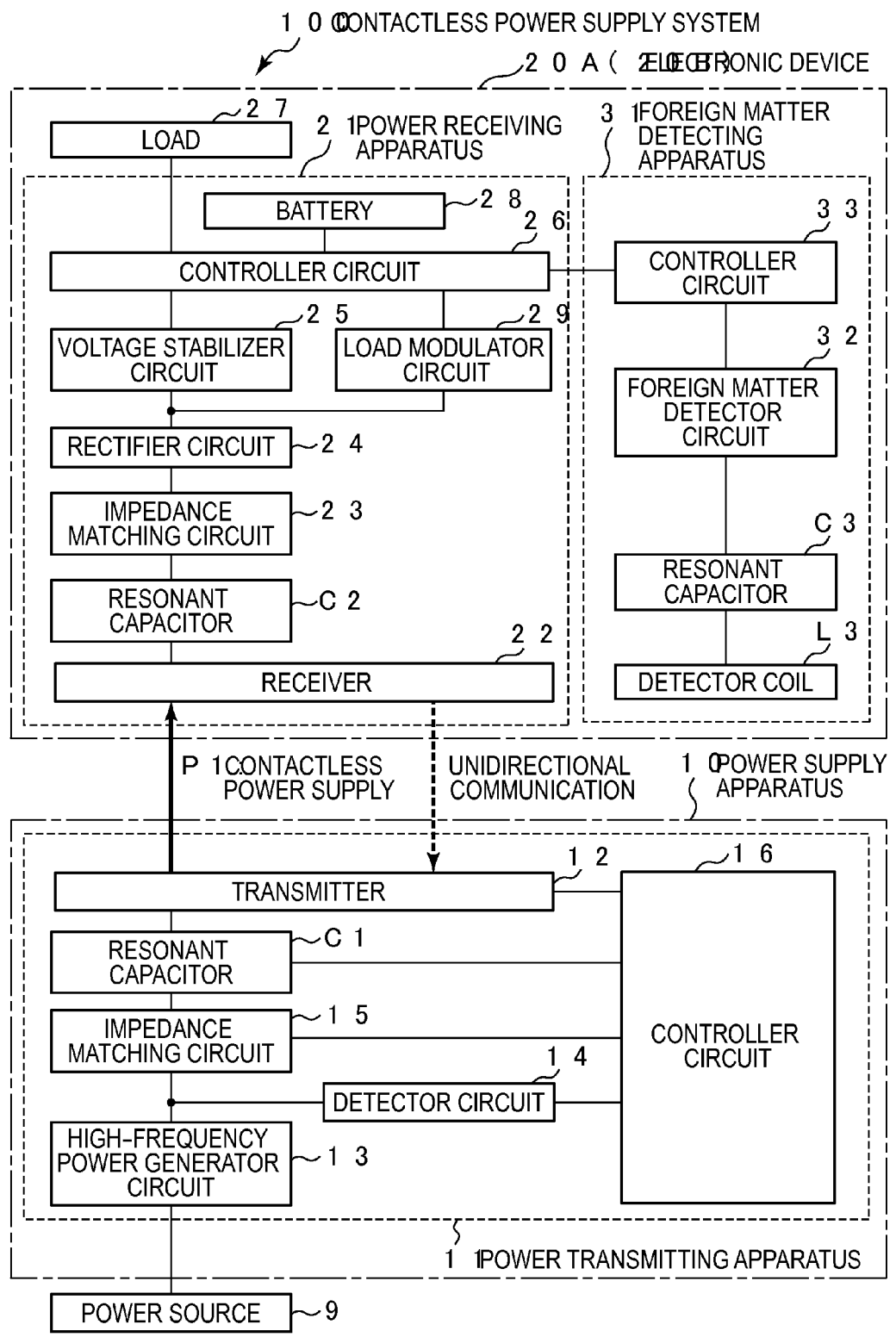
FIG. 3 is a block diagram illustrating an exemplary configuration of a contactless power supply system according to the first embodiment of the present disclosure.
Figure 4:
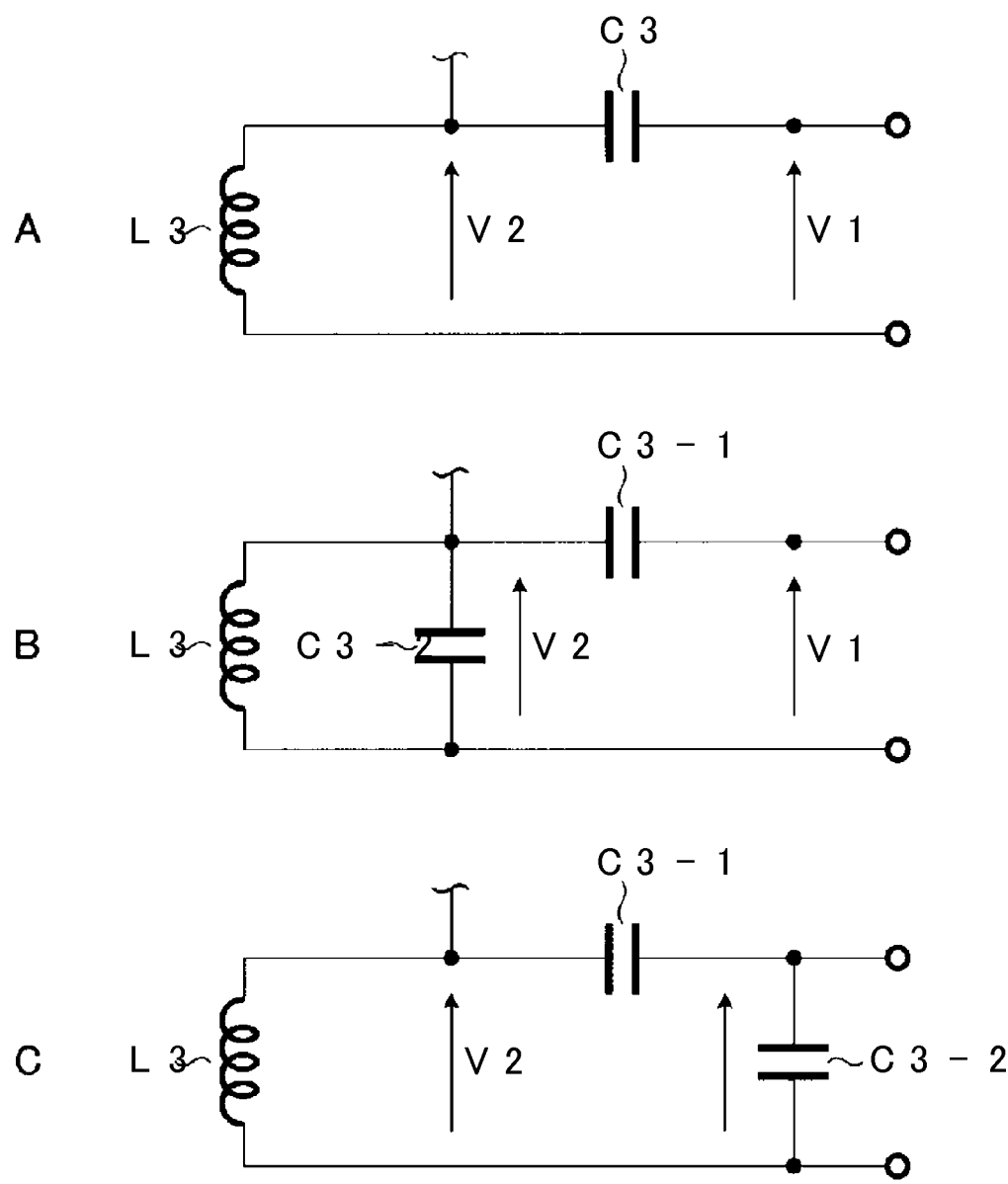
FIGS. 4A to 4C are circuit diagrams illustrating exemplary configurations of a resonant circuit.

FIG. 2 illustrates an exemplary diagrammatic configuration of a contactless power supply system given as a magnetic coupling system according to the first embodiment of the present disclosure, while FIG. 3 illustrates an exemplary block configuration of a contactless power supply system according to the first embodiment of the present disclosure.

The contactless power supply system 100 illustrated in FIG. 2 is a system that transfers (supplies) power in a contactless manner using a magnetic field (in the present embodiment, using magnetic resonance). The contactless power supply system 100 is equipped with a power supply apparatus 10 (the primary device) and one or multiple electronic devices (secondary devices) given as power recipient devices. Herein, an electronic device 20A in the form of a mobile phone handset and an electronic device 20B in the form of a digital still camera are provided as power recipient devices, for example. However, a power recipient device is not limited to this example, and may be any electronic device able to receive power from the power supply apparatus 10 in a contactless manner.

As illustrated in FIG. 2, for example, the contactless power supply system 100 is configured such that power is transferred from the power supply apparatus 10 to the electronic devices 20A and 20B by placing the electronic devices 20A and 20B onto or in proximity to a power supply surface (transmitter surface) S1 of the power supply apparatus 10. Herein, the power supply apparatus 10 has a mat shape (or tray shape) with the surface area of the power supply surface S1 being greater than devices such as the power recipient electronic devices 20A and 20B, in consideration of the case of transferring power to multiple electronic devices 20A and 20B simultaneously or in a time division (successively).

(Exemplary Configuration of Power Supply Apparatus)

As described above, the power supply apparatus 10 is an apparatus (such as a charging tray) that transfers power to electronic devices 20A and 20B using a magnetic field. As illustrated in FIG. 3, for example, the power supply apparatus 10 is equipped with a power transmitting apparatus 11 that transfers power using power supplied from a power source 9 external to the power supply apparatus 10. The external power source 9 may be, for example, an electric utility from which power is supplied via a plug socket, otherwise called a power outlet.

The power transmitting apparatus 11 includes a transmitter 12, a high-frequency power generator circuit 13, a detector circuit 14, an impedance matching circuit 15, a controller circuit 16, and a resonant capacitor (capacitive element) C1, for example. By providing the detector circuit 14 and the controller circuit 16, the power transmitting apparatus 11 in this example takes a block configuration enabling the contactless power supply system 100 to conduct unidirectional communication using load modulation. However, the configuration is not limited thereto in cases where unidirectional communication using a technique other than load modulation or bidirectional communication is considered.

Figure 5:
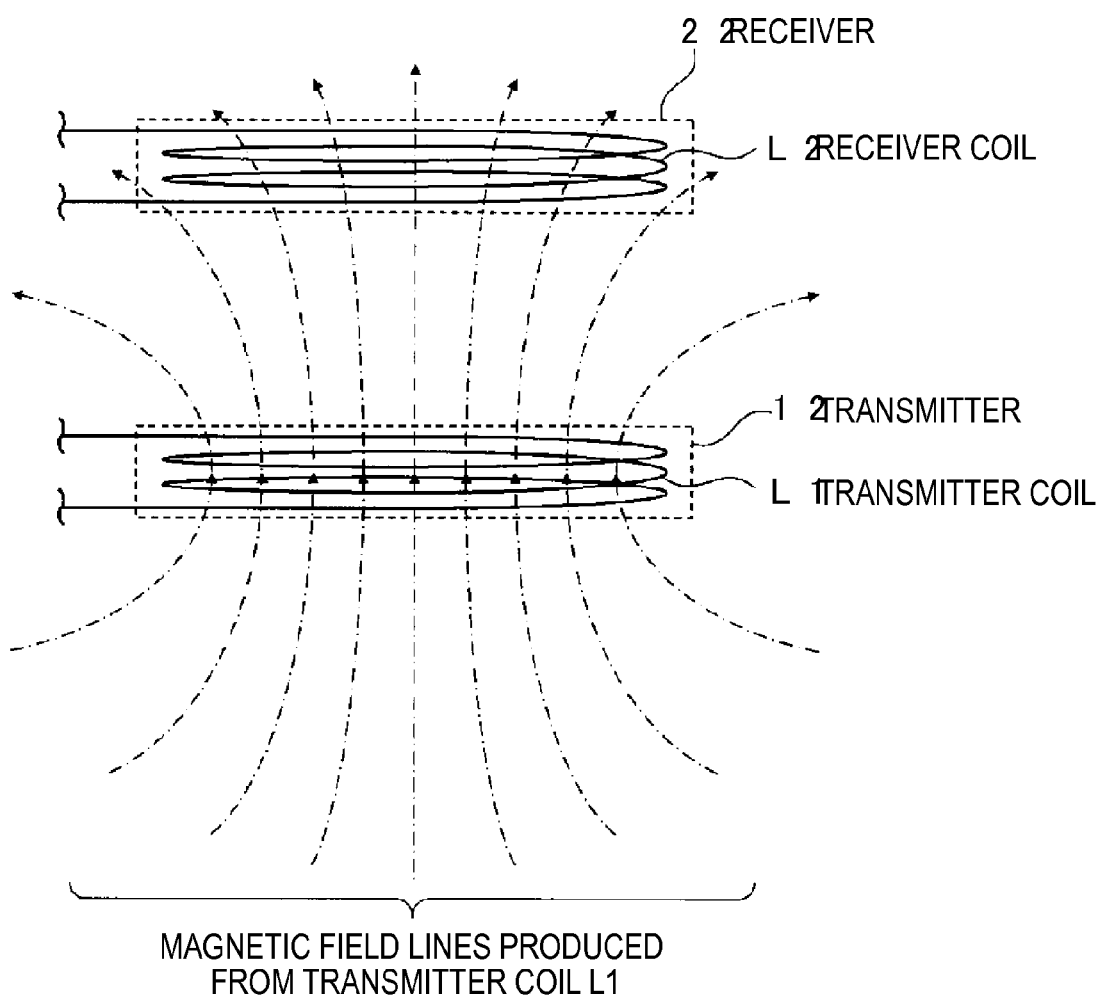
FIG. 5 is a schematic diagram of an exemplary diagrammatic configuration of a transmitter coil and a receiver coil in a contactless power supply system according to the first embodiment of the present disclosure.

The transmitter 12 includes components such as a transmitter coil (primary coil) L1 discussed later (FIG. 5). The transmitter 12 uses the transmitter coil L1 and the resonant capacitor C1 to transfer power to the electronic devices 20A and 20B (specifically, to a receiver 22 discussed later) using a magnetic field. Specifically, the transmitter 12 includes functionality for emitting a magnetic field (magnetic flux) from the power supply surface S1 towards the electronic devices 20A and 20B. A detailed configuration of the transmitter 12 will be discussed later.

The high-frequency power generator circuit 13 is a circuit that uses power supplied from the power source 9 external to the power supply apparatus 10 to generate given high-frequency power (an AC signal) for the purpose of power transfer, for example.

The detector circuit 14 is a circuit that includes functionality for detecting (demodulating) a modulated signal from a load modulator circuit 29 discussed later. The detector circuit 14 supplies detection results to the controller circuit 16.

The impedance matching circuit 15 is a circuit that matches impedance during power transfer. In so doing, efficiency during power transfer (the transfer efficiency) is improved. Note that, depending on the configuration of components such as the transmitter coil L1 and a receiver coil L2 discussed later, or the resonant capacitors C1 and C2, it may also be configured such that the impedance matching circuit 15 is not provided. Also, if decreased transfer efficiency is not a concern, it may be configured such that the impedance matching circuit 15 is not provided.

The resonant capacitor C1 is a capacitive element constituting part of the transmitter coil L1 of the transmitter 12 as well as the LC resonator (resonant circuit), and is disposed with respect to the transmitter coil L1 so as to form an electrical series connection, parallel connection, or a combined series and parallel connection. With an LC resonator including the transmitter coil L1 and the resonant capacitor C1, resonant operation is realized at a resonant frequency (first resonant frequency) f1 whose frequency is approximately equal or near that of the high-frequency power generated in the high-frequency power generator circuit 13. The capacitance value of the resonant capacitor C1 is also set so as to obtain such a resonant frequency f1.

However, it may also be configured such that the resonant capacitor C1 is not provided if the above resonant frequency f1 is realized by resonant operation using a potential difference across the windings in the transmitter coil L1 or a parasitic capacitance component (stray capacitance component) realized by a potential difference between the transmitter coil L1 and the receiver coil L2 discussed later. Also, if decreased transfer efficiency is not a concern, it may be similarly configured such that the resonant capacitor C1 is not provided.

The controller circuit 16 is a circuit that receives detection results from the detector circuit 14 and controls components such as the high-frequency power generator circuit 13, the impedance matching circuit 15, the resonant capacitor C1, and the transmitter 12.

For example, consider the case where foreign metal is detected between the transmitter 12 and the receiver 22 by a foreign matter detecting apparatus 31 discussed later in the electronic devices 20A and 20B. At this point, the detection result from the detector circuit 14 changes due to load modulation conducted in the load modulator circuit 29, also discussed later, in the electronic devices 20A and 20B. For this reason, the controller circuit 16 in the power transmitting apparatus 11 is able to confirm the presence of foreign metal, making it possible to restrict or stop power transfer under control by the controller circuit 16. Meanwhile, the controller circuit 16 also receives detection results from the detector circuit 14 and applies pulse-width modulation control (PWM control) to the high-frequency power generator circuit 13 and switching control to the impedance matching circuit 15, the resonant capacitor C1, and the transmitter 12. Such control by the controller circuit 16 also enables automatic control for maintaining a high transfer efficiency (power supply efficiency).

(Exemplary Configuration of Electronic Device)

Electronic devices such as stationary electronic devices typified by televisions or portable electronic devices typified by mobile phones and digital cameras, including rechargeable batteries, are applicable as the electronic devices 20A and 20B. The electronic device 20A and the electronic device 20B are provided with similar functionality with respect to power supply, and in the description hereinafter, the electronic device 20A will be described as a representative example.

As illustrated in FIG. 3, for example, the electronic device 20A is equipped with a power receiving apparatus 21 and a load 27 that performs given action (action that elicits functionality as an electronic device) on the basis of power supplied from the power receiving apparatus 21. The electronic device 20A is also equipped with a foreign matter detecting apparatus 31 for detecting the presence of foreign metal between (in the gap between) the transmitter 12 and the receiver 22.

Hereinafter, the power receiving apparatus 21 will be described.

The power receiving apparatus 21 includes a receiver 22, a resonant capacitor (capacitive element) C2, an impedance matching circuit 23, a rectifier circuit 24, a voltage stabilizer circuit 25, a controller circuit 26, a battery 28, and a load modulator circuit 29. By providing the load modulator circuit 29 and the controller circuit 26, the power receiving apparatus 21 in this example takes a block configuration enabling the contactless power supply system 100 to conduct unidirectional communication using load modulation. However, the configuration is not limited thereto in cases where unidirectional communication using a technique other than load modulation or bidirectional communication is considered.

The receiver 22 includes components such as a receiver coil (secondary coil) L2 discussed later (FIG. 5). The receiver 22 includes functionality for using the receiver coil L2 and the resonant capacitor C2 to receive power transferred from the transmitter 12 in the power supply apparatus 10. A detailed configuration of the receiver 22 will be discussed later.

The resonant capacitor C2 is a capacitive element constituting part of the receiver coil L2 of the receiver 22 as well as the LC resonator (resonant circuit), and is disposed with respect to the receiver coil L2 so as to form an electrical series connection, parallel connection, or a combined series and parallel connection. With an LC resonator including the receiver coil L2 and the resonant capacitor C2, resonant operation is realized at a resonant frequency (second resonant frequency) f2 whose frequency is approximately equal or near that of the high-frequency power generated in the high-frequency power generator circuit 13 of the power transmitting apparatus 11. In other words, the LC resonator including the transmitter coil L1 and the resonant capacitor C1 in the power transmitting apparatus 11 and the LC resonator including the receiver coil L2 and the resonant capacitor C2 in the power receiving apparatus 21 resonate with each other at approximately equal resonant frequencies (f1≈f2). The capacitance value of the resonant capacitor C2 is also set so as to obtain such a resonant frequency f2.

However, it may also be configured such that the resonant capacitor C2 is also not provided if the above resonant frequency f1 is realized by resonant operation using a potential difference across the windings in the receiver coil L2 or a parasitic capacitance component realized by a potential difference between the transmitter coil L1 and the receiver coil L2. Also, if decreased transfer efficiency is not a concern, it may also be configured such that the resonant frequency f2 and the resonant frequency f1 differ from each other (f2 f1), and the resonant capacitor C2 is not provided.

The impedance matching circuit 23 is a circuit that matches impedance during power transfer, similarly to the impedance matching circuit 15 in the above power transmitting apparatus 11. Note that, depending on the configuration of components such as the transmitter coil L1 and the receiver coil L2 discussed later, or the resonant capacitors C1 and C2, it may also be configured such that the impedance matching circuit 23 is also not provided. Also, if decreased transfer efficiency is not a concern, it may be similarly configured such that the impedance matching circuit 23 is also not provided.

The rectifier circuit 24 is a circuit that rectifies the power (AC power) supplied from the receiver 22 to generate direct current (DC) power. Note that a smoothing circuit (not illustrated) for smoothing rectified power is often provided between the rectifier circuit 24 and the voltage stabilizer circuit 25 discussed later.

The voltage stabilizer circuit 25 is a circuit that conducts given voltage stabilization on the basis of DC power supplied from the rectifier circuit 24, and charges the battery 28 or a battery (not illustrated) in the load 27.

The battery 28 stores power in response to being charged by the voltage stabilizer circuit 25, and may be realized using a rechargeable battery (secondary cell) such as a lithium-ion battery, for example. Note that the battery 28 may also be omitted in cases where only the battery in the load 27 is used, for example.

The load modulator circuit 29 is a circuit for applying load modulation, and changes in the power state due to load modulation may be detected with the detector circuit 14 in the power transmitting apparatus 11. In other words, if given the load modulator circuit 29 and the controller circuit 26 discussed later, it becomes possible to transmit information in the power receiving apparatus 21 to the power transmitting apparatus 11 without providing a special communication apparatus in the electronic device 20A.

The controller circuit 26 is a circuit for controlling charging operation with respect to the battery 28 or the battery (not illustrated) in the load 27. The controller circuit 26 is also a circuit for controlling load modulation in the load modulator circuit 29, and applies control enabling the power transmitting apparatus 11 to recognize that foreign metal has been detected by having changes in the power state due to such load modulation be detected with the detector circuit 14 in the power transmitting apparatus 11. Additionally, in the case where the foreign matter detecting apparatus 31 discussed later in the electronic device 20A detects that foreign metal is present between the transmitter 12 and the receiver 22, it is also possible for the controller circuit 26 to apply charging control to restrict or stop power transfer to the power receiving apparatus 21 in the electronic device 20A.

Hereinafter, the foreign matter detecting apparatus 31 will be described.

The foreign matter detecting apparatus 31 includes a detector coil L3, a resonant capacitor C3, a foreign matter detector circuit 32, and a controller circuit 33. As an example, the foreign matter detector circuit 32 and the controller circuit 33 may constitute a detector.

The detector coil L3 is an example of a magnetic coupling element for detecting foreign metal, and is provided separately from the transmitter coil L1 and the receiver coil L2. Further details will be discussed later (FIGS. 4, 6, 7, 13-16, and 17-19).

The resonant capacitor C3 is a capacitor connected to the detector coil L3 in an electrical series configuration (see FIG. 4A), or a capacitor connected to the detector coil L3 in a combined electrical series and parallel configuration (resonant capacitors C3-1 and C3-2) (see FIGS. 4B and 4C). By connecting the resonant capacitor C3, the detector coil L3 resonates at a given frequency f3 (LC resonance).

Note that in the case of computing the Q factor of the LC resonator (resonant circuit) from the voltage ratio as discussed later, it is desirable to connect at least one resonant capacitor C3 to the detector coil L3 in series (see FIGS. 4A, 4B, and 4C). However, in the case of computing the Q factor of the LC resonator with a technique other than voltage ratio, such as with a width at half maximum (WHM) method, the resonant capacitor C3 may be connected to the detector coil L3 in an electrical parallel configuration (not illustrated).

The foreign matter detector circuit 32 is a circuit for measuring the Q factor of the detector coil L3 or the Q factor of the LC resonator (a resonant circuit) including the detector coil L3 and the resonant capacitor C3 by using an AC signal whose frequency (f3, where f3≠f2 and f3≠f2) differs from the frequencies (f1 and f2, where f1≈f2) of the AC signals flowing through the transmitter coil L1 and the receiver coil L2.

The Q factor of the detector coil L3 or the Q factor of the LC resonator including the detector coil L3 and the resonant capacitor C3 may be computed by measuring voltage values at the two locations (the voltage value V1 and the voltage value V2) illustrated in FIGS. 4A, 4B, and 4C as described earlier with the foreign matter detector circuit 32, and then taking their ratio (V2/V1), for example.

Also, if the frequency characteristics related to properties such as the impedance and admittance are able to be measured with the foreign matter detector circuit 32, it is also possible to compute the Q factor of the detector coil L3 or the LC resonator from the ratio of the peak frequency at which the frequency characteristics reach a peak versus the frequency width where that peak value is halved (WHM) (thus, peak frequency/WHM).

Additionally, it is also possible to calculate the Q factor from the ratio of the real part versus the imaginary part of the impedance of the resonant circuit. The real part and the imaginary part of the impedance may be computed using an auto-balancing bridge circuit and a vector ratio detector, for example.

The controller circuit 33 is a circuit that controls the foreign matter detector circuit 32, while also determining the presence of foreign metal between (in the gap between) the transmitter 12 and the receiver 22 from the measurement results by the foreign matter detector circuit 32. The controller circuit 33 is also a circuit for transmitting the determination result to the controller circuit 26 of the power receiving apparatus 21. The controller circuit 33 may, for example, compare a measured Q factor to a threshold value saved in memory (not illustrated) in advance, and determine that foreign metal is present near the detector coil in the case where the measured Q factor is less than the threshold value.

[Detailed Exemplary Configuration of Transmitter and Receiver]

FIG. 5 is a schematic illustration of an exemplary diagrammatic configuration of the transmitter 12 and the receiver 22 in a contactless power supply system according to the first embodiment of the present disclosure.

The transmitter 12 includes at least one (in this case, one) transmitter coil L1, and the receiver 22 includes at least one (in this case, one) receiver coil L2. It is possible for the transmitter coil L1 and the receiver coil L2 to be magnetically coupled to each other. Note that it may also be configured such that the transmitter 12 and the receiver 22 includes one or multiple coils or one or multiple LC resonators (resonant circuits) including coils and capacitors in addition to the transmitter coil L1 and the receiver coil L2.

These coils (the transmitter coil L1 and the receiver coil L2) are not limited to being open coils (conductive coils) shaped like conductive wire (material) wound multiple times, but may also be open loops (conductive loops) shaped like conductive wire wound one time.

Furthermore, the coil or loop used as such a conductive coil or conductive loop may be a coil (wound coil) or loop (wound loop) in which conductive wire is wound, or a coil (patterned coil) or loop (patterned loop) formed by a conductive pattern on a printed substrate (printed circuit board) or flexible printed substrate (flexible printed circuit board), for example. Also, it is possible to form such a patterned coil and patterned loop by printing or depositing conductive material, or by machining a conductive metal plate or sheet, for example.

FIG. 5 simultaneously illustrates an exemplary distribution of magnetic field lines produced from the transmitter coil L1 at a given phase. As described above, the transmitter coil L1 is a coil for transferring power using magnetic flux (lines of magnetic force; a magnetic field). In other words, the transmitter coil L1 is a coil for producing magnetic flux (lines of magnetic force; a magnetic field). Meanwhile, the receiver coil L2 is a coil for receiving power from the magnetic flux (lines of magnetic force; a magnetic field) transferred from the transmitter 12.

[Detailed Exemplary Configuration of Detector Coil]

Figure 6:
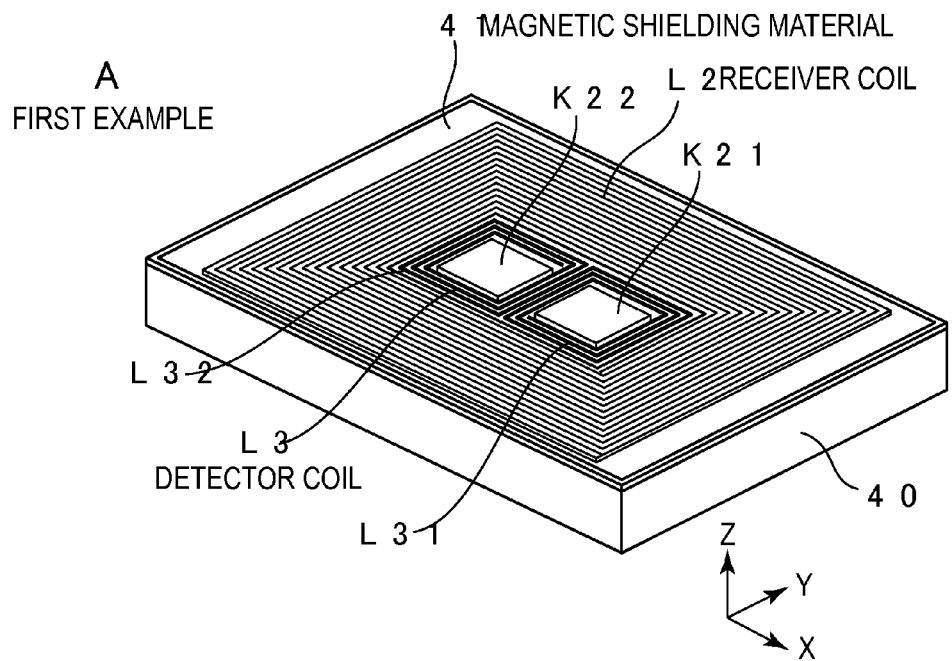
FIG. 6 is an explanatory diagram illustrating an exemplary detailed configuration of a detector coil and receiver coil according to the first embodiment of the present disclosure, where
Figure 6:
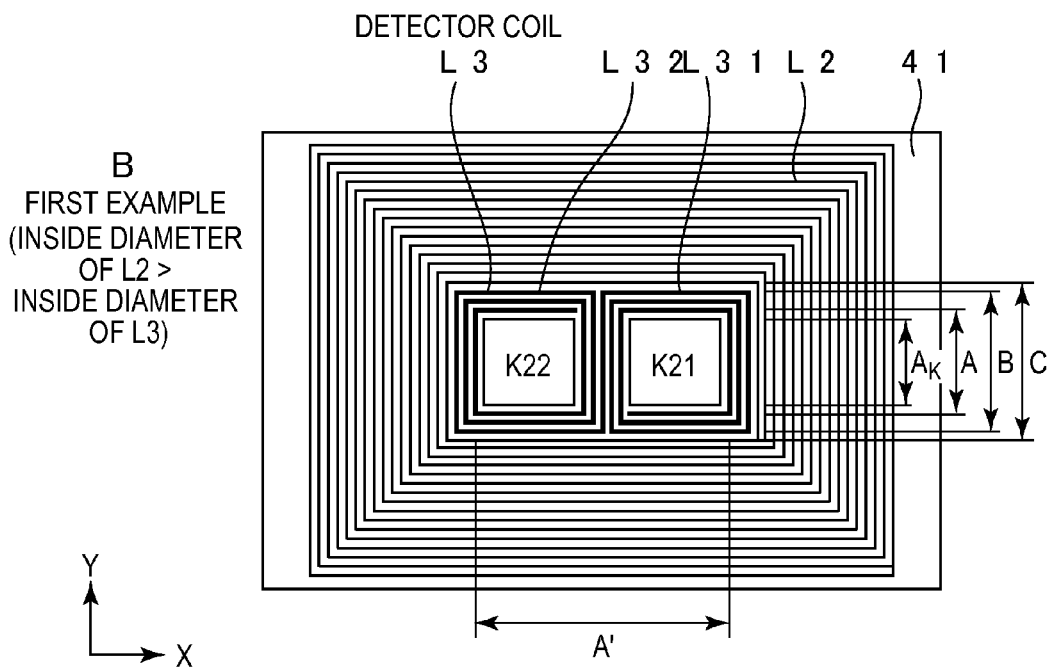

FIG. 6 is an illustration of an exemplary detailed configuration of the detector coil L3 and the receiver coil L2 according to the first embodiment of the present disclosure, where FIG. 6A is an exemplary perspective view configuration and FIG. 6B is an exemplary plan view configuration (exemplary X-Y plan view configuration).

As illustrated in FIGS. 6A and 6B, magnetic shielding material 41 is disposed between the housing 40 of the electronic device, and the receiver coil L2 and detector coil L3. Also, the detector coil L3 is disposed in the center of the receiver coil L2. Positioning units K21 and K22 are respectively disposed in the inner vicinity of the coil L31 and the coil L32 constituting the detector coil L3. In this example, the outer dimension $A_K$ of the positioning units K21 and K22 is smaller than the inner dimension A of the coils L31 and L32.

In order to decrease magnetic flux leakage from the receiver coil L2 and the detector coil L3, and also to raise the Q factor of the receiver coil L2 and detector coil L3, it is desirable to realize the magnetic shielding material 41 with magnetic material such as ferrite, conductive metal such as metal, or a combination of magnetic material and conductive metal, for example.

Meanwhile, it is desirable to realize the positioning unit K21 and the positioning unit K22 with magnetic material in order to raise the Q factor of the detector coil L3. However, the magnetic shielding material 41, the positioning unit K21, and the positioning unit K22 may be any material used to maintain the shape and placement of the detector coil L3 and the receiver coil L2, such as a bonding agent, adhesive, bonding tape, or laminate. For example, materials such as plastic, glass, and wood are also acceptable.

Additionally, in the case where the magnetic shielding material 41, the positioning unit K21, and the positioning unit K22 are realized with magnetic material, it is desirable from a manufacturing cost standpoint for these magnetic materials to have approximately the same composition. From another standpoint, however, in some cases it may also be desirable to differentiate the composition of at least one or more of these magnetic materials from the composition of the other magnetic materials.

The receiver coil L2 illustrated in FIG. 6 is a spiral-shaped coil. In order to effectively raise the magnetic coupling between the transmitter coil L1 and the receiver coil L2, it is desirable for the transmitter coil L1 and the receiver coil L2 to be spiral-shaped coils, helical coils, or coils with a combined spiral and helical shape, for example. However, the transmitter coil L1 and the receiver coil L2 are not limited thereto.

Figure 7:
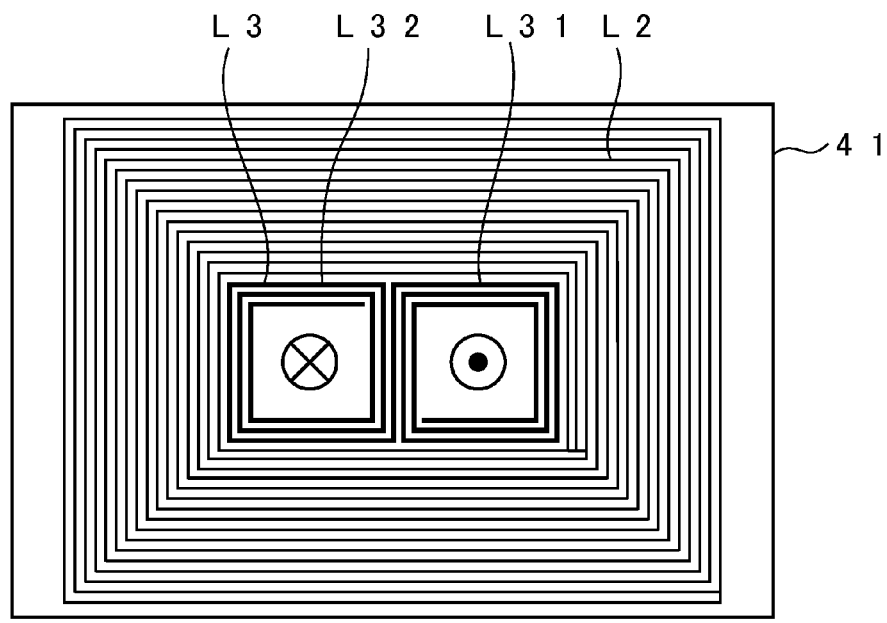
FIG. 7 is a plan view illustrating an exemplary configuration (exemplary X-Y plan view configuration) of a detector coil and a receiver coil according to a comparative example.
Figure 8:
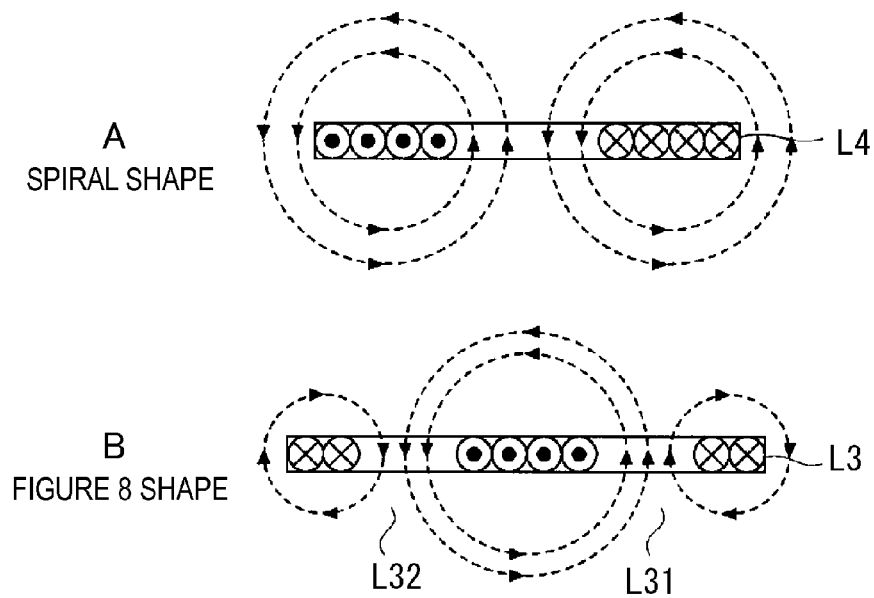

Also, the detector coil L3 illustrated in FIG. 6 is a figure 8-shaped coil realized by a combination of a spiral-shaped coil L31 and a spiral-shaped coil L32 (see FIG. 7) that distributes magnetic flux of approximately the opposite orientation of the orientation of the magnetic flux from the coil L31. Although details will be discussed later, if the detector coil L3 is simply a spiral-shaped coil, helical coil, or a coil with a combined spiral and helical shape, foreign metal detection accuracy may greatly decrease. For this reason, it is desirable for the detector coil L3 to be a coil able to distribute magnetic flux (magnetic field lines; a magnetic field) over a surface with approximately opposing orientations, such as a figure 8-shaped, square grid-shaped, or lattice-shaped coil as discussed later.

Although details will likewise be discussed later, using a detector coil with such a shape yields advantages such as enabling decreased magnetic flux leakage from the detector coil, decreased change in the electrical properties (such as the Q factor and L value) of the detector coil due to external factors, and a decrease in unwanted noise occurring in the detector coil. For this reason, it is possible to greatly improve foreign metal detection accuracy.

Furthermore, the coil or loop used as the detector coil L3 may be a coil (wound coil) or loop (wound loop) in which conductive wire is wound, or a coil (patterned coil) or loop (patterned loop) formed by a conductive pattern on a printed substrate (printed circuit board) or flexible printed substrate (flexible printed circuit board), for example. Also, it is possible to form such a patterned coil and patterned loop by printing or depositing conductive material, or by machining a conductive metal plate or sheet, for example.

Also, while the receiver coil L2 and the detector coil L3 may be disposed in the same plane, the receiver coil L2 and the detector coil L3 may also be disposed in different planes. However, for the sake of the packaging area with respect to the electronic device 20A (20B), in many cases it is desirable to form the receiver 22 (receiver coil L2) and the detector coil L3 in the same plane.

Additionally, in FIG. 6, the inner dimension (the dimension of the innermost perimeter) of the detector coil L3 is smaller than the inner dimension C (the dimension of the innermost perimeter) of the receiver coil L2, and the outer dimension B (the dimension of the outermost perimeter) of the detector coil L3 is smaller than the inner dimension C (the dimension of the innermost perimeter) of the receiver coil L2. Although details will be discussed later, such a configuration maximally raises the foreign metal detection accuracy. Obviously, however, the configuration is not limited thereto in applications where foreign metal detection accuracy is not demanded.

Note that although FIG. 6 compared the inner dimension A and the outer dimension B along the shorter edge of the figure 8-shaped detector coil L3 to the inner dimension C along the shorter edge of the receiver coil L2, the dimensions may also be compared using the respective inner dimensions and outer dimensions along the longer edge (such as the inner dimension A' along the longer edge of the detector coil L3, for example). It is further desirable if the inner dimension and outer dimension along both the shorter edge and the longer edge of the detector coil are smaller than the inner dimensions along both the shorter edge and the longer edge of the receiver coil. Obviously, however, the configuration is not limited thereto in applications where foreign metal detection accuracy is not demanded.

Additionally, although it is desirable for the detector coil L3 to be electrically insulated from (i.e., not connected to an electrical contact point or other element in) the transmitter 12 (transmitter coil L1) and the receiver 22 (receiver coil L2), the configuration is not limited thereto.

(Distribution of Magnetic Field Lines in Detector Coil)

The distribution of magnetic field lines in the detector coil L3 will now be described with reference to FIG. 8.

FIG. 8A is a diagrammatic cross-section view regarding a spiral-shaped coil of the related art (such as the detector coil L4, for example) at a given time (phase) and the distribution of magnetic field lines produced from that coil. FIG. 8B is a diagrammatic cross-section view regarding a figure 8-shaped coil (such as the detector coil L3, for example) at a given time (phase) and the distribution of magnetic field lines produced from that coil. Note that, for the sake of convenience, FIG. 8B illustrates the distribution of magnetic field lines produced by a detector coil L3 in a state where positioning units K21 and K22 are not disposed.

As illustrated in FIGS. 8A and 8B, the distribution of magnetic field lines differs greatly between a spiral-shaped coil and a figure 8-shaped coil.

In the case of a spiral-shaped detector coil L4, magnetic field lines are more easily distributed farther near the edges of the detector coil L4. For this reason, there is significant magnetic flux leakage from the detector coil L4, and the electrical properties (such as the Q factor and L value) of the detector coil L4 change greatly due to external factors (such as the metal material or magnetic material constituting the transmitter coil L1, the receiver coil L2, the magnetic shielding material 41, the power supply apparatus 10, and the electronic device 20A (20B)). In other words, foreign metal detection accuracy is greatly decreased in the case of using a spiral-shaped coil as the detector coil.

On the other hand, the figure 8-shaped coil discussed above is configured to be able to distribute magnetic flux (magnetic field lines; a magnetic field) over a surface such that the magnetic flux from the two coils (the coils L31 and L32, for example) constituting the figure 8-shaped coil have approximately opposing orientations. As a result, in the figure 8-shaped coil, magnetic field lines are distributed so as to form a loop inside the coil. In other words, in the figure 8-shaped coil, the magnetic field lines are less likely to be distributed farther compared to a spiral-shaped coil.

For this reason, using the figure 8-shaped detector coil L3 yields less magnetic flux leakage from the detector coil L3, and the electrical properties (such as the Q factor and L value) of the detector coil L3 change less due to external factors (such as the metal material or magnetic material constituting the transmitter coil L1, the receiver coil L2, the magnetic shielding material 41, the power supply apparatus 10, and the electronic device 20A (20B)) compared to the spiral-shaped detector coil L4. Thus, foreign metal detection accuracy is greatly improved in the case of using a figure 8-shaped coil as the detector coil compared to the case of using a spiral-shaped coil.

Experiments were conducted to acquire data related to the detector coil Q factor by applying electromagnetic field analysis to an analysis model of the detector coils L3 and L4 and a receiver coil like those illustrated in FIGS. 6A, 6B, and 8A. The acquired data indicates to what degree the Q factors of the detector coils L3 and L4 change depending on the presence or absence of the receiver coil L2 in the case of modifying the inner dimension of the detector coils L3 and L4. However, when modifying the inner dimension of the detector coil L3, factors such as the conductive wire type, thickness, width, and the length of the gap between conductive wires constituting the detector coil L3 are not modified.

According to an experiment, we obtained a result that in the case of using a figure 8-shaped detector coil L3, although the Q factor of the detector coil L3 does change slightly depending on whether or not the receiver coil L2 is present, the magnitude of that change is significantly smaller than in the case of using the spiral-shaped detector coil L4. In other words, although the Q factor of the detector coil L3 does change slightly due to the presence of the receiver coil L2, the magnitude of that change is significantly smaller than in the case of using the spiral-shaped detector coil L4. This indicates that for the figure 8-shaped detector coil L3, there is less magnetic flux leakage from the detector coil L3, and the electrical properties (such as the Q factor and L value) of the detector coil L3 change less due to external factors (such as the metal material or magnetic material constituting the transmitter coil L1, the receiver coil L2, the magnetic shielding material 41, the power supply apparatus 10, and the electronic device 20A (20B)) compared to the spiral-shaped detector coil L4.

Stated differently, in the case of using a figure 8-shaped coil as the detector coil, foreign metal detection accuracy is greatly improved compared to the case of using a spiral-shaped coil. Furthermore, as the inner dimension A of the detector coil L3 becomes smaller with respect to the inner dimension C of the receiver coil L2 (for example, if the difference between the detector coil inner dimension A and the receiver coil inner dimension C becomes less than or equal to 0 mm), the amount of decrease in the Q factor of the detector coil L3 due to the presence of the receiver coil L2 also becomes smaller.

In addition, there is a result obtained that the Q factor of the detector coil L3 is greatest (maximized) in the case where the difference between the detector coil inner dimension A and the receiver coil inner dimension C is −4 mm, for example, and in the case where the difference between the detector coil inner dimension A and the receiver coil inner dimension C is 0 mm. In other words, it may be desirable for the inner dimension A of the detector coil L3 to be smaller than the inner dimension C of the receiver coil L2.

Also, since the difference in the Q factor of the detector coil L3 depending on whether or not the receiver coil L2 is present becomes smaller as the inner dimension A of the detector coil L3 becomes smaller with respect to the inner dimension C of the receiver coil L2, it may be desirable for the outer dimension B of the detector coil L3 also to be smaller than the inner dimension C of the receiver coil L2. However, the configuration is not limited thereto in the case where it is desirable to extend the foreign metal detection range even if the foreign metal detection accuracy drops.

[Action and Advantages of Contactless Power Supply System]

1. Summary of Overall Operation

In the power supply apparatus 10 of the contactless power supply system 100, the high-frequency power generator circuit 13 supplies given high-frequency power (an AC signal) for transferring power to the transmitter coil L1 and the resonant capacitor C1 (LC resonator) in the transmitter 12. In so doing, a magnetic field (magnetic flux) is produced in the transmitter coil L1 in the transmitter 12. At this point, if an electronic device 20A given as a power recipient (charging target) is placed (or brought near) the top surface (power supply surface S1) of the power supply apparatus 10, the transmitter coil L1 in the power supply apparatus 10 and the receiver coil L2 in the electronic device 20A come into proximity near the power supply surface S1.

In this way, if a receiver coil L2 is placed near a transmitter coil L1 producing a magnetic field (magnetic flux), electromotive force, induced by the magnetic flux produced from the transmitter coil L1, is produced in the receiver coil L2. In other words, the transmitter coil L1 and the receiver coil L2 are respectively linked by electromagnetic induction or magnetic resonance, and a magnetic field is produced. In so doing, power (indicated as the contactless power supply P1 in FIG. 3) is transferred from the transmitter coil L1 (primary coil; power supply apparatus 10; transmitter 12) to the receiver coil L2 (secondary coil; electronic device 20A; receiver 22). At this point, resonant operation using the transmitter coil L1 and the resonant capacitor C1 is conducted in the power supply apparatus 10 (at a resonant frequency f1), while resonant operation using the receiver coil L2 and the resonant capacitor C2 is conducted in the electronic device 20A (at a resonant frequency f2, where f2≈f1).

Thereupon, AC power received by the receiver coil L2 in the electronic device 20A is supplied to the rectifier circuit 24 and the voltage stabilizer circuit 25, and the following charging operation is performed. Namely, after the AC power is converted into given DC power by the rectifier circuit 24, voltage stabilization based on the DC power is performed by the voltage stabilizer circuit 25, and the battery 28 or a battery (not illustrated) in the load 27 is charged. In so doing, charging operation based on power received by the receiver 22 is performed in the electronic device 20A.

In other words, in the present embodiment, a terminal connection to an AC adapter, for example, is unnecessary when charging the electronic device 20A, and charging may be easily initiated (contactless power supply may be performed) by simply placing the electronic device 20A onto (or in proximity to) the power supply surface S1 of the power supply apparatus 10. This leads to a reduced burden on the user.

Meanwhile, in the foreign matter detecting apparatus 31 of the electronic device 20A, the Q factor of a detector coil L3 or an LC resonator (a resonant circuit) including the detector coil L3 and a resonant capacitor C3 is measured using an AC signal whose frequency (f3, where f3≠f2 and f3≠f2) differs from the frequencies (f1 and f2) of the AC signals flowing through the transmitter coil L1 and the receiver coil L2. The foreign matter detecting apparatus 31 is also able to determine the presence of foreign metal between (in the gap between) the transmitter 12 and the receiver 22 from the magnitude of change in this Q factor.

Subsequently, a determination result by the foreign matter detecting apparatus 31 which indicates the presence or absence of foreign metal is transmitted from the power receiving apparatus 21 in the electronic device 20A to the power transmitting apparatus 11 in the power supply apparatus 10 by a communication technique such as load modulation.

Furthermore, in the case where the foreign matter detecting apparatus 31 detects the presence of foreign metal between (in the gap between) the transmitter 12 and the receiver 22, control for restricting or stopping power transfer is applied by the controller circuit 16 in the power transmitting apparatus 11 or the controller circuit 26 in the power receiving apparatus 21, for example. As a result, it may be possible to preemptively avoid heat produced in the foreign metal, as well as malfunction or damage to the contactless power supply system.

2. Action of Detector Coil

Next, action of the detector coil L3 given as a characteristic feature of the present embodiment will be described in detail and in comparison to comparative examples (examples of the related art).

2.1 Case of Detector Coil According to Comparative Example

FIG. 7 illustrates an exemplary configuration (exemplary X-Y plan view configuration) of a detector coil L3 and a receiver coil L2 according to a comparative example. Although magnetic shielding material 41 is disposed in FIG. 7, the positioning unit K21 and the positioning unit K22 are not disposed, unlike FIG. 6.

If affixing the detector coil L3 and the receiver coil L2 to the magnetic shielding material 41 in the case of a configuration like that of FIG. 7, it is difficult to accurately affix the components with a desired placement. Also, there is a high possibility that the placement of the magnetic shielding material 41, the detector coil L3, and the receiver coil L2 may change if the affixing strength weakens between the magnetic shielding material 41 and the detector coil L3 or the receiver coil L2 due to some factor such as long-term deterioration or impact, and particularly in the case where the components become unfixed. Furthermore, issues such as a change in the relative placement between the magnetic shielding material 41 and the detector coil L3 or the receiver coil L2, a change in the relative placement of the detector coil L3 and the receiver coil L2, or a change in the relative placement of multiple coils (in this case, two coils) constituting the detector coil L3 may lead to a change in the foreign metal detection accuracy.

2.2 Detector Coil According to First Embodiment

In contrast, in the present embodiment, a positioning unit K21 and a positioning unit K22 are disposed on the inner side of the coil L31 and the coil L32 constituting the detector coil L3, as illustrated by the example in FIG. 6. The relative placement of other components is the same as that of the comparative example illustrated in FIG. 7.

If affixing the detector coil L3 and the receiver coil L2 to the magnetic shielding material 41 with such a layout, it is possible to affix the components with a desired placement more accurately than in the comparative example. Specifically, the detector coil L3 and the receiver coil L2 are affixed to the magnetic shielding material 41 according to a sequence like that illustrated by the example in FIGS. 9A, 9B, 9C, and 9D.

Figure 9:
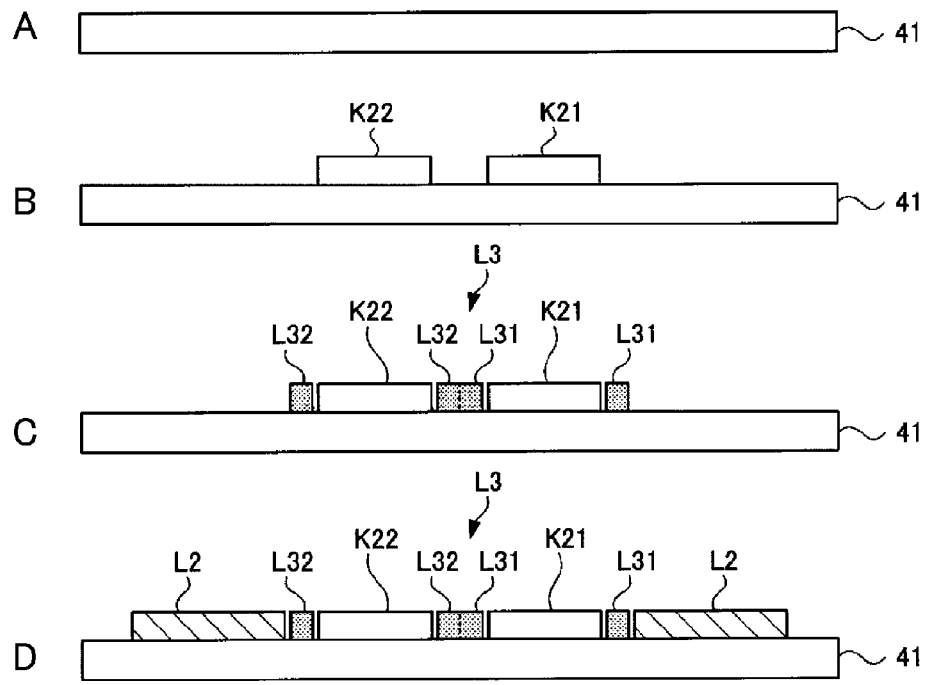
FIGS. 9A to 9D are explanatory diagrams illustrating manufacturing stages for a detector coil and a receiver coil according to the first embodiment of the present disclosure.

First, the magnetic shielding material 41 is disposed, as illustrated in FIG. 9A.

Next, the positioning unit K21 and the positioning unit K22 are disposed on and affixed to the magnetic shielding material 41, as illustrated in FIG. 9B. However, the magnetic shielding material 41 and at least one of the positioning unit K21 and the positioning unit K22 may have a unitary construction, and in this case, it is possible to omit the step illustrated in FIG. 9A. Such a case is often preferable since the accuracy of placement between the magnetic shielding material 41 and the positioning units K21 and K22 is increased.

The detector coil L3 is then disposed and affixed using the placement of the positioning unit K21 and the positioning unit K22 as guides, as illustrated in FIG. 9C. Specifically, the outermost portions of the positioning unit K21 and the positioning unit K22 are aligned with the innermost perimeter of the detector coil L3. For this reason, placement accuracy increases to the degree that the dimension of the outermost portions (the outer dimension) of the positioning unit K21 and the positioning unit K22 is close to the dimension of the innermost perimeter of the detector coil L3.

Lastly, the receiver coil L2 is disposed and affixed using the placement of the detector coil L3 as a guide, as illustrated in FIG. 9D. Specifically, the outermost portion of the detector coil L3 is aligned with the innermost perimeter of the receiver coil L2. For this reason, placement accuracy increases to the degree that the dimension of the outermost portion of the detector coil L3 is close to the dimension of the innermost perimeter of the detector coil L3.

In this way, by following a sequence like the above, it is possible to dispose components such as the magnetic shielding material 41, the detector coil L3, multiple coils (in this example, the coils L31 and L32) constituting the detector coil L3, as well as the receiver coil L2 with extremely high positional precision. In other words, it is possible to accurately dispose a detector coil used to detect foreign matter at a desired position. As a result, detection accuracy variations among individual foreign matter detecting systems is mitigated. It is also possible to reduce detection accuracy variations due to issues such as the placement of foreign metal.

The sequence in FIGS. 9A, 9B, 9C, and 9D described above is merely one example, and other sequences may also be used. However, it is desirable to dispose the positioning unit K21 and the positioning unit K22 in the inner region of the two coils constituting the detector coil L3.

At this point, if the positioning unit K21 and the positioning unit K22 are realized with magnetic material, it becomes possible to improve the Q factor of the detector coil. However, at least one of the positioning unit K21 and the positioning unit K22 may be realized with magnetic material, rather than both the positioning unit K21 and the positioning unit K22.

Taking f to be the frequency at which the electrical properties (electrical parameters) of the detector coil are measured, L to be the inductance value of the detector coil at the measuring frequency, and R to be the resistance value of the detector coil at the measuring frequency, the Q factor, or quality coefficient, of the detector coil may be expressed by the formula:

$$Q=(2\pi f L)/R$$

Additionally, in cases such as when the positioning unit K21 and the positioning unit K22 are realized with magnetic material, the hysteresis loss (the imaginary part $\mu''$ of the permeability) of the magnetic material is very small, and the effective permeability (the real part $\mu'$ of the permeability) is very large, the increase in the inductance value L of the detector coil due to disposing magnetic material is greater than the increase in the resistance value R. Thus, it becomes possible to improve the Q factor of the detector coil by adjusting such parameters. In other words, it is desirable that the magnetic material used for the positioning unit K21 and the positioning unit K22 cause a greater increase in the inductance value L of the detector coil than the resistance value R.

Note that it is desirable to establish a relationship of $\mu'>\mu''$, particularly $\mu'>>\mu''$, between the real part $\mu'$ and the imaginary part $\mu''$ of the permeability of the magnetic material.

2.3 Measured Data

Figure 10:
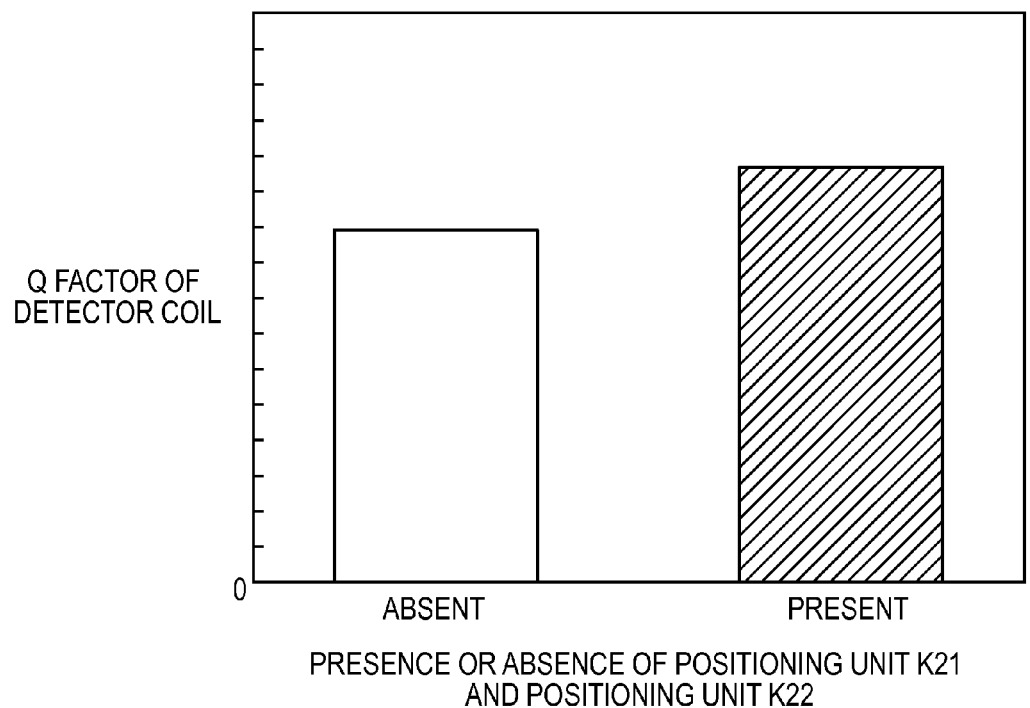
FIG. 10 is a graph illustrating an example of the difference in the Q factor of a detector coil according to whether or not two positioning units are present.

FIG. 10 is a graph regarding the first embodiment, illustrating an example of the difference in the Q factor of the detector coil L3 according to whether or not two positioning units are present.

FIG. 10 illustrates experimental data for the case where the positioning unit K21 and the positioning unit K22 are made up magnetic material, and illustrates the change in the Q factor of the detector coil L3 according to whether or not the positioning unit K21 and the positioning unit K22 are present. The experimental data also demonstrates that by having the positioning unit K21 and the positioning unit K22 present, the Q factor of the detector coil L3 improves by approximately 20%. In other words, since applying a configuration according to the present embodiment improves the Q factor of the detector coil itself, which is particularly important for detecting foreign matter, it is possible to improve the foreign metal detection accuracy. Note that it is still possible to further improve the Q factor of the detector coil L3, depending on the permeability ($\mu'$, $\mu''$) of the magnetic material constituting the positioning unit K21 and the positioning unit K22, the shape and configuration of the detector coil L3.

Action and Advantages of First Embodiment

According to the first embodiment described above, action and advantages like the following are obtained.

For example, if the first embodiment is applied foreign matter detection systems using magnetic coupling elements, detection accuracy variations among individual foreign matter detection systems is mitigated. It is also possible to reduce detection accuracy variations due to issues such as the placement of foreign matter. This is because using positioning units makes it possible to accurately dispose magnetic coupling elements used to detect foreign matter at desired positions with respect to a contactless power supply coil.

Meanwhile, the foreign matter detection accuracy also improves in a foreign matter detection system that detects the presence of foreign metal on the basis of changes in the Q factor of an LC resonator (resonant circuit) that at least includes a magnetic coupling element, or of the magnetic coupling element itself. This is because applying the present embodiment makes it possible to improve the Q factor of the magnetic coupling element itself, which is particularly important for detecting foreign matter.

Thus, it becomes possible to detect foreign metal or other foreign matter which may generate heat due to magnetic flux without providing an additional sensor, and furthermore greatly improve detection accuracy.

Note that in a contactless power supply system that aligns a primary device and a secondary device by using a magnet disposed inside either the primary device or the secondary device, and magnetic material disposed inside the other device, it is possible to use the magnetic material utilized in the present embodiment (such as for the positioning units K21, K22, and K3, for example) jointly as the magnetic material for such alignment.

Also, in the case of using one or multiple magnetic coupling elements (detector coils) that include multiple coils for a foreign matter detecting apparatus, it is desirable to dispose positioning units on the inner sides of at least two or more of the multiple coils constituting the one or multiple magnetic coupling elements. This is in order to dispose components such as the magnetic shielding material, magnetic coupling elements, multiple coils constituting the magnetic coupling elements, as well as the receiver coil with extremely high positional precision, as discussed earlier.

However, this does not exclude disposing a positioning unit on the inner side of only one coil from among the multiple coils constituting the one or multiple magnetic coupling elements. For example, only one of the positioning units K21 and K22 may be disposed in the examples in FIGS. 6 and 11, while only one of the raised sections K3a and K3b may be disposed in the example in FIG. 12. The positioning functionality of a positioning unit is still valid even in the case of disposing a positioning unit on the inner side of only one coil.

Additionally, among the positioning units disposed on the inner side of at least two or more coils of the multiple coils constituting the one or more magnetic coupling elements, it is desirable to realize at least one or more positioning units with magnetic material.

Moreover, it is particularly desirable to dispose a positioning unit on the inner side of all coils constituting the one or more magnetic coupling elements, and to realize all of those positioning units with magnetic material.

3. Second Embodiment

Figure 11:
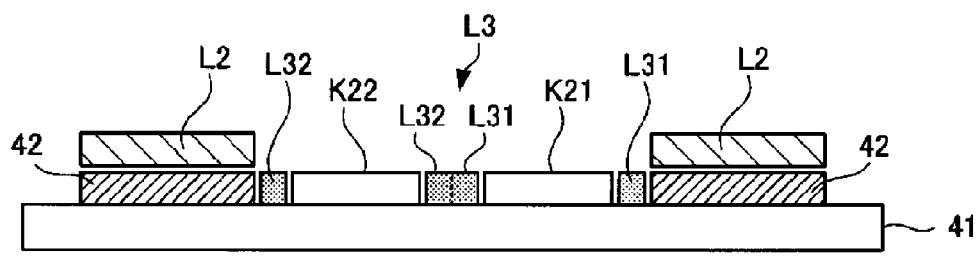
FIG. 11 is a diagrammatic cross-section view illustrating an exemplary configuration of a detector coil and a receiver coil according to the second embodiment of the present disclosure.

FIG. 11 is a diagrammatic cross-section view illustrating an exemplary configuration of a detector coil and a receiver coil according to the second embodiment of the present disclosure.

First, the magnetic shielding material 41 is disposed, and the positioning unit K21 and the positioning unit K22 are disposed and affixed on top of to the magnetic shielding material 41, as illustrated in FIGS. 9A to 9C. The detector coil L3 is then disposed and affixed using the placement of the positioning unit K21 and the positioning unit K22 as guides.

After that, magnetic material 42 is disposed using the placement of the detector coil L3 as a guide. Specifically, the outermost portion of the detector coil L3 is aligned with the innermost perimeter of the magnetic material 42. The receiver coil L2 is then disposed and affixed on top of the magnetic material 42.

According to the second embodiment described above, it is possible to dispose components such as magnetic shielding material, a detector coil, multiple coils constituting a detector coil, magnetic material, and a receiver coil with extremely positional precision, similarly to the first embodiment.

4. Third Embodiment

Figure 12:
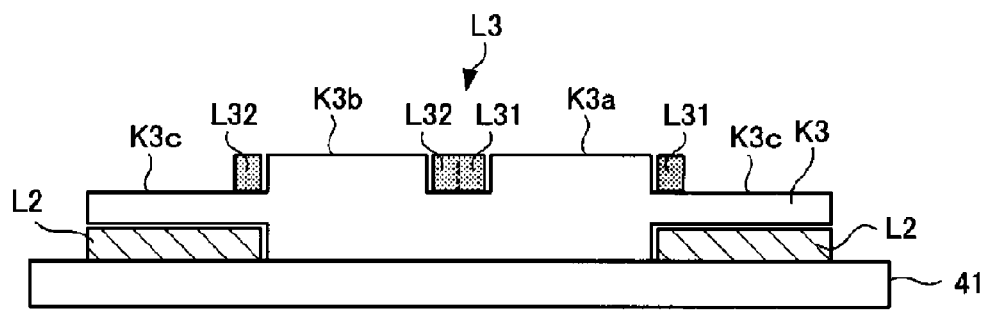
FIG. 12 is a diagrammatic cross-section view illustrating an exemplary configuration of a detector coil and a receiver coil according to the third embodiment of the present disclosure.

FIG. 12 is a diagrammatic cross-section view illustrating an exemplary configuration of a detector coil and a receiver coil according to the third embodiment of the present disclosure. The present embodiment is an example in which positioning units and other components are disposed after disposing the receiver coil.

First, the magnetic shielding material 41 is disposed, and the receiver coil L2 is disposed and affixed on top of the magnetic shielding material 41. For example, the receiver coil L2 may be disposed and affixed on top of the magnetic shielding material 41 using a laminate. Alternatively, the receiver coil L2 may be disposed and affixed on top of the magnetic shielding material 41 using double-sided adhesive tape with adhesive applied on both sides thereof.

Next, a positioning unit K3 is disposed and affixed on the inner side of the receiver coil L2, using the innermost perimeter of the receiver coil L2 as a guide.

The positioning unit K3 may have a rectangular or elliptical shape as viewed from above, for example, in correspondence with the spiral-shaped receiver coil L2. Two raised sections K3a and K3b which function as positioning units are formed on the part of the top of the positioning unit K3. These two raised sections K3a and K3b are structured to fit into the inner sides of the coil L31 and the coil L32 constituting the detector coil L3.

The detector coil L3 is then disposed and affixed on top of the positioning unit K3, using the two raised sections K3a and K3b on top of the positioning unit K3 as guides. Specifically, the respective outermost portions of the two raised sections K3a and K3b formed on the positioning unit K3 are aligned with the innermost perimeter of the detector coil L3.

According to the third embodiment described above, it is possible to dispose components such as magnetic shielding material, a detector coil, multiple coils constituting a detector coil, and a receiver coil with extremely positional precision, similarly to the first embodiment.

Note that although positioning units are all disposed on the inner sides of the windings of the multiple coils constituting a magnetic coupling element (detector coil) in the first through third embodiments, it may also be configured such that a positioning unit is disposed nearby on the outer side of the windings of at least one coil.

For example, in FIGS. 9A and 9B, the positioning units K21 and K22 may be respectively disposed and affixed nearby on the outer side of the coils L31 and L32. In this case, a space sufficient to dispose the positioning units is provided between the detector coil L3 and the receiver coil L2.

As another example, in FIG. 12, an approximately ring-shaped raised section (not illustrated) may be provided on the planar section K3c of the positioning unit K3, nearby on the outer side of the outermost perimeter of the coils L31 and L32, so as to enclose the coils L31 and the L32. In this case, the inner perimeter of the raised section on the planar section K3c of the positioning unit K3 is aligned with the outermost perimeter of the coils L31 and L32.

Also, in the case of disposing a positioning unit on the outer side of the windings of a single coil, at least one or more bar-shaped or parallelepiped-shaped positioning units, for example, may be disposed on the outer side of some portion of the outermost perimeter of the coil, rather than enclosing the outermost perimeter of the coil as described above. To take the detector coil L3 (FIG. 7) as an example, it may also be configured such that positioning units are respectively disposed on the outer side of the outermost perimeter on two sides of the approximately square detector coil L3 (for a total of two positioning units). Furthermore, providing respective positioning units on the outer side of the outermost perimeter on four sides of the detector coil L3 (for a total of four positioning units) makes it possible to position the detector coil L3 in not only one direction but also the direction orthogonal thereto, and is thus more preferable.

The first through third embodiments have been described using an example of detecting foreign matter while contactless power supply is in operation. However, an embodiment of the present disclosure is not limited only to such cases, and various modifications are possible. For example, it is also conceivable that contactless power supply operation may be suspended or that power supplied by contactless power supply may be restricted while detecting foreign matter.

Since the unwanted noise produced in the detector coil decreases in such cases, it is not strictly necessary to make the frequency of the AC signal flowing through the detector coil differ from the frequencies of the AC signals flowing through the transmitter coil and the receiver coil. In other words, foreign matter detection may be conducted using an AC signal whose frequency is approximately equal to the frequencies (f1≈f2) of the AC signals used for contactless power supply operation. Also, in such cases particularly it is also possible to make the detector coil the same as the transmitter coil or the receiver coil.

Modification 1

Figure 13:
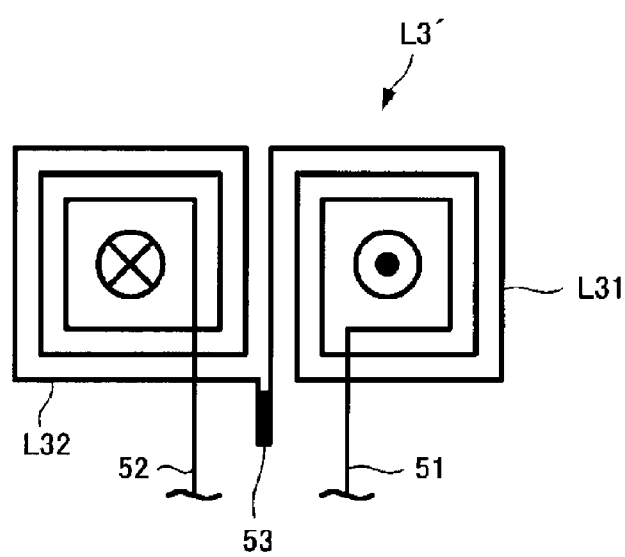
FIG. 13 is a plan view illustrating an exemplary configuration of a figure 8-shaped detector coil according to a first modification of the first through third embodiments of the present disclosure.

Although the foregoing first through third embodiments have been described for the case of using a continuous figure 8-shaped detector coil as illustrated in FIGS. 6 and 7, a figure 8-shaped detector coil (magnetic coupling element) like that illustrated in FIG. 13 may also be used as an example of the first modification.

In the example in FIG. 13, a figure 8-shaped detector coil L3' includes spiral-shaped coils L31 and L32, with one end of the coil L31 being electrically connected (joined) in series to one end of the coil L32 using solder or a connector, for example. However, the coils L31 and L32 are connected such that the magnetic flux (magnetic field lines) produced from the coil L31 and the magnetic flux (magnetic field lines) produced from the coil L32 have approximately opposing orientations, as illustrated by FIG. 8B and the example in FIG. 13.

Note that this connection may also be an electrical parallel connection or a combined series and parallel connection.

For example, in the case of an electrical series connection, voltage may be measured using a lead 51 from the coil L31 and a lead 52 from the coil L32. In the case of an electrical parallel connection, voltage may be measured between the junction 53 of the coil L31 and the lead 51 or between the junction 53 of the coil L32 and the coil L32, taking the junction 53 between the coil L31 and the coil L32 as a reference potential point.

According to the first modification, since simple spiral-shaped coils are joined to constitute a figure 8-shaped detector coil, the electrical properties of the two coils may be easily made nearly equal compared to a continuous figure 8-shaped coil.

Although the foregoing first through third embodiments and the first modification thereof have been described an example of the case of applying a single magnetic coupling element (figure 8-shaped coil) made up of two coils to a detector coil as an example of the first embodiment of the present disclosure, the present disclosure is not limited to the foregoing embodiment, and various modifications are possible.

For example, in some cases it may be desirable to use one or multiple magnetic coupling elements shaped like multiple coils electrically connected together, in order to improve foreign matter detection accuracy, for example.

In other words, in order to further improve foreign matter detection accuracy, for example, it may be more desirable to use one or multiple magnetic coupling elements shaped like multiple coils electrically connected together, in which the magnetic flux produced from at least one or more of these multiple coils and the magnetic flux produced from the remaining of these multiple coils have approximately opposing orientations.

Hereinafter, examples of other embodiments of the present disclosure will be described with reference to the drawings. Note that structural elements like those of the first embodiment and the first modification thereof are denoted with the same reference numerals, and repeated explanation of these structural elements is omitted.

Modification 2

The configuration is not limited to a figure 8-shaped coil according to the first through third embodiments and the first modification thereof, and a square grid-shaped (in other words, a 2×2 lattice-shaped) coil may also be used as a detector coil (magnetic coupling element). Hereinafter, an example applying a square grid-shaped coil to the detector coil will be described as the second modification of the first through third embodiments of the present disclosure.

Figure 14:
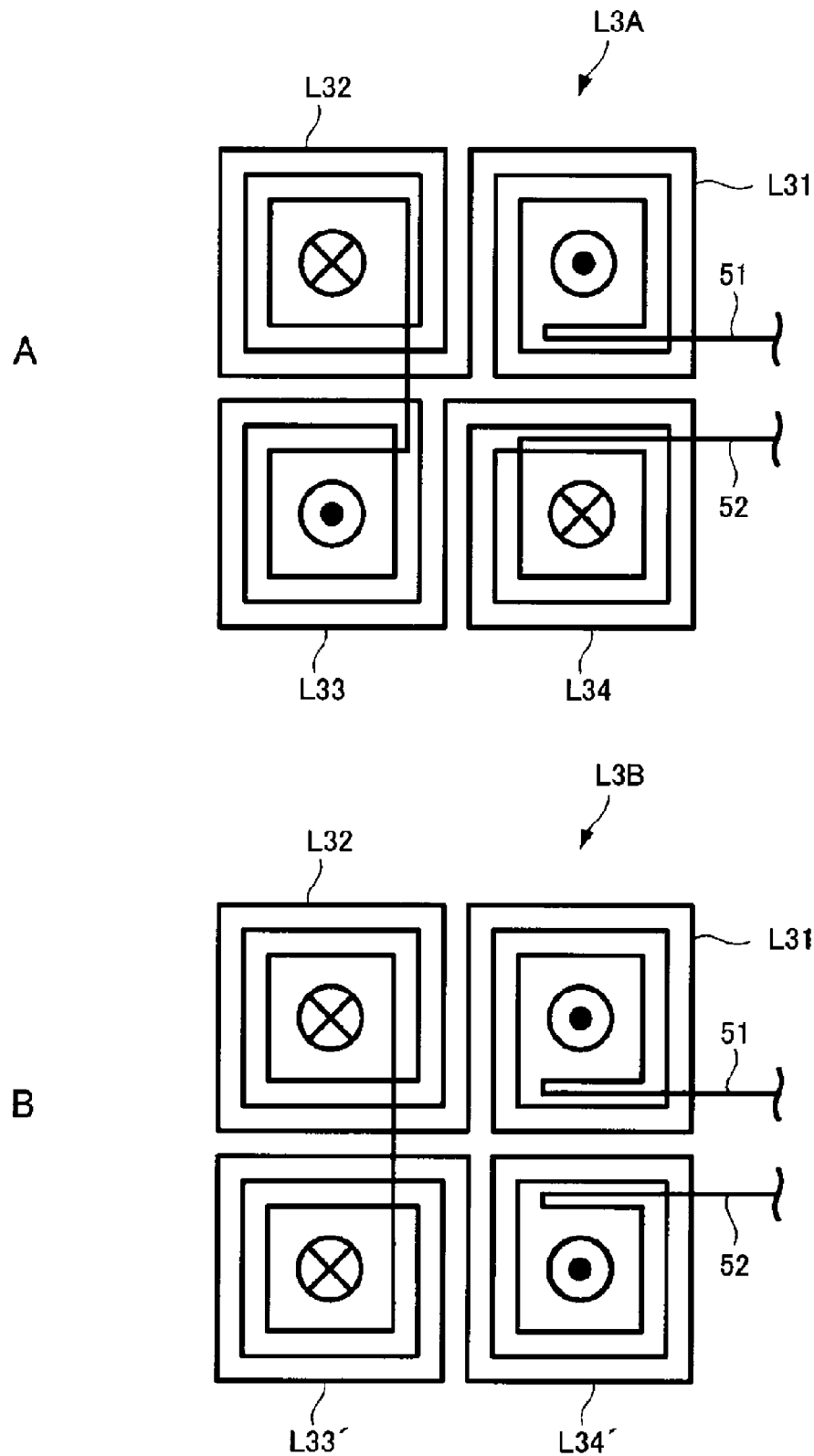
FIG. 14 is an explanatory diagram illustrating an exemplary configuration of a square grid-shaped detector coil according to a second modification of the first through third embodiments of the present disclosure, where

FIG. 14 is an explanatory diagram illustrating an exemplary configuration of a square grid-shaped detector coil according to the second modification of the first through third embodiments of the present disclosure.

The square grid-shaped detector coil L3A (the first example) shown in FIG. 14A includes four spiral-shaped coils L31 to L34 electrically connected (joined) in series. The coils L33 and L34 have a mostly similar configuration to the spiral-shaped coils L31 and L32. The coil L31 includes a lead 51, while the coil L34 includes a lead 52. The coil L32 and the coil L33 do not have leads, and are electrically connected to their respectively adjacent coils L31 and L34. In the detector coil L3A in this example, the coils L31 to L34 are connected such that the magnetic flux (magnetic field lines) produced from the coils L31 and L33 is of approximately opposite orientation to the magnetic flux (magnetic field lines) produced from the coils L32 and L34 at a given time (phase).

The square grid-shaped detector coil L3B (the second example) shown in FIG. 14B differs from the detector coil L3A in that the coils constituting the detector coil L3B are connected such that the magnetic flux (magnetic field lines) produced from the coils L31 and L34' on which leads 51 and 52 are formed is of approximately opposite orientation to the magnetic flux (magnetic field lines) produced from the coils L32 and L33' at a given time (phase).

Note that this connection shown in FIGS. 14A and 14B may also be an electrical parallel connection or a combined series and parallel connection, similarly to the example in FIG. 13.

In the second modification, it is likewise desirable for the relationship between the inner dimension A or the outer dimension B of the detector coil L3A and the receiver coil to be the relationship described in the first embodiment.

According to the second modification of the first through third embodiments discussed above, action and advantages like the following are obtained in addition to the action and advantages of the first through third embodiments.

A detector coil according to the second modification is a square grid-shaped coil including four coils. Increasing the number of coils compared to the figure 8-shaped coil according to the first through third embodiments increases the surface area occupied by the detector coil and increases the detection range. For example, in the case of a detector coil according to the second modification, the detection range may be doubled compared to a detector coil of the first through third embodiments.

However, since a detector coil of the first through third embodiments and the first modification thereof has better detection accuracy, the decision to implement the first through third embodiments (including the first modification) or the second modification may be determined according to whether detection accuracy or detection range is prioritized.

Third Embodiment

The configuration is not limited to a square grid-shaped coil according to the second modification of the first through third embodiments above, and a lattice-shaped coil may also be used as a detector coil (magnetic coupling element). Hereinafter, an example applying a lattice-shaped coil to the detector coil will be described as a third modification of the first through third embodiments of the present disclosure.

Figure 15:
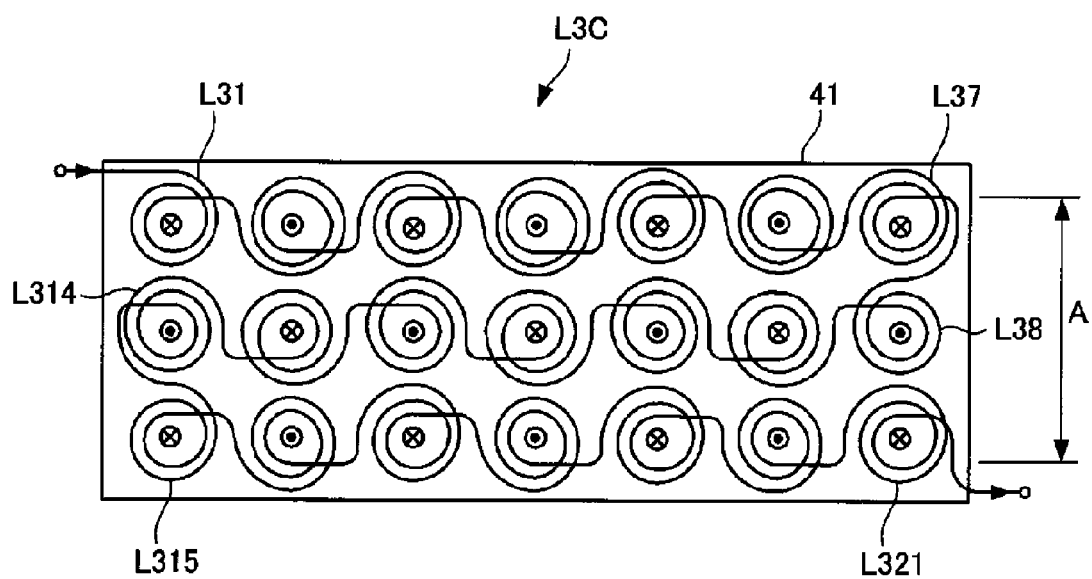
FIG. 15 is a plan view illustrating an exemplary configuration of a lattice-shaped detector coil according to a third modification of the first through third embodiments of the present disclosure.

FIG. 15 is a plan view illustrating an exemplary configuration of a lattice-shaped detector coil according to the third modification of the first through third embodiments of the present disclosure.

The lattice-shaped detector coil L3C is configured such that multiple coils are connected in an electrical series connection, parallel connection, or a combined series and parallel connection. The example in FIG. 15 is for the case of a detector coil that includes 21 spiral-shaped coils L31 to L321 connected in series.

In the detector coil L3C, the coils L31 to L321 are disposed in a matrix parallel to the plane of the magnetic shielding material 41, for example, with the coils from the coil L31 to the coil L321 being continuously connected in sequence. For example, the coils L31 to L37 may be connected from left to right, with the coils L38 to L314 connected from right to left on the next row down, and the coils L315 to L321 connected from left to right one more row down. The coils L31 to L321 are connected such that the magnetic flux (magnetic field lines) produced from adjacent coils are of approximately opposing orientations at a given time (phase).

In this way, a detector coil may be configured such that multiple coils such as spiral-shaped coils, helical coils, or coils with a combined spiral and helical shape (in other words, coils having a basic ring shape) are connected in an electrical series connection, parallel connection, or a combined series and parallel connection. However, it is desirable for these multiple coils constituting the detector coil to be connected such that the magnetic flux (magnetic field lines) produced from at least one or more of these multiple coils and the magnetic flux (magnetic field lines) produced from the remaining of these multiple coils have approximately opposing orientations at a given time (phase).

Also, in the case where the detector coil includes multiple coils, it is particularly desirable for the total magnetic flux (magnetic field lines) produced from at least one or more coils to be approximately equal to the total magnetic flux (magnetic field lines) of approximately opposite orientation produced from the remaining coils. In this case, issues such as magnetic flux leakage from the detector coil, changes in the electrical properties (electrical parameters) of the detector coil due to external factors, and unwanted noise occurring in the detector coil decrease particularly. In order to equalize the total magnetic flux, it is desirable for there to be an even number of coils constituting the detector coil in the case where each of the multiple coils has approximately the same shape.

Furthermore, it is desirable for the number of coils producing magnetic flux (magnetic field lines) of approximately opposite orientation to be half the number of coils constituting the detector coil. In this case, since the magnetic flux distribution within the detector coil becomes approximately uniform, foreign metal detection accuracy stabilizes.

Meanwhile, it is desirable for at least one or more coils from among the multiple coils constituting the detector coil to have an inner dimension that is smaller than the inner dimension of the transmitter coil or the receiver coil.

In addition, it is desirable for the overall inner dimension of the multiple coils constituting the detector coil to be smaller than the inner dimension of the transmitter coil or the receiver coil. The overall inner dimension of the multiple coils constituting the detector coil may be either the inner dimension A along the shorter edge or the inner dimension A' along the longer edge, as illustrated in FIG. 15.

Furthermore, it is particularly desirable for the overall outer dimension of the detector coil to be smaller than the inner dimension of the transmitter coil or the receiver coil.

These parameters are for decreasing change in the electrical properties (such as the Q factor and L value) of the detector coil due to external factors.

Also, in order to effectively suppress unwanted noise produced in the detector coil, it is desirable for the shape of the detector coil to be an approximately symmetrical shape, such as by having approximate rotational symmetry, approximate line symmetry, or approximate point symmetry. However, the configuration is not limited thereto in the case where it is desirable to extend the foreign metal detection range even if the foreign metal detection accuracy drops.

According to the third modification of the first through third embodiments discussed above, the number of coils constituting the detector coil is further increased compared to the second modification of the first through third embodiments, and thus the detection range of the detector coil is significantly extended.

Fourth Embodiment

Figure 16:
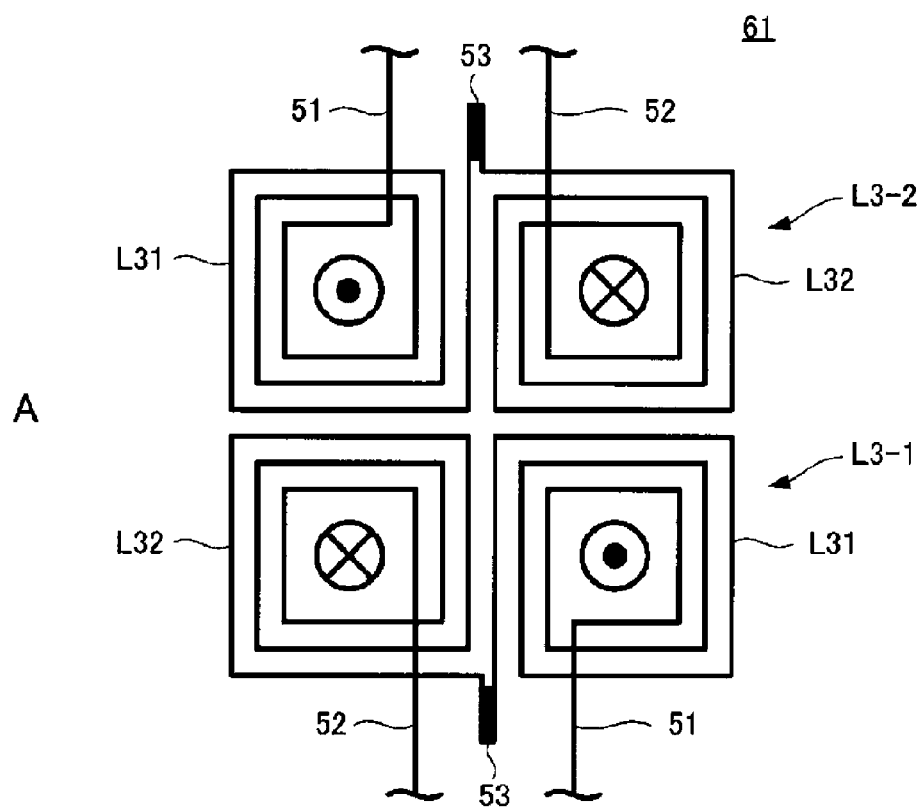
FIG. 16 is an explanatory diagram for a detector coil unit in which two figure 8-shaped detector coils are disposed according to a fourth modification of the first through third embodiments of the present disclosure, where
Figure 16:
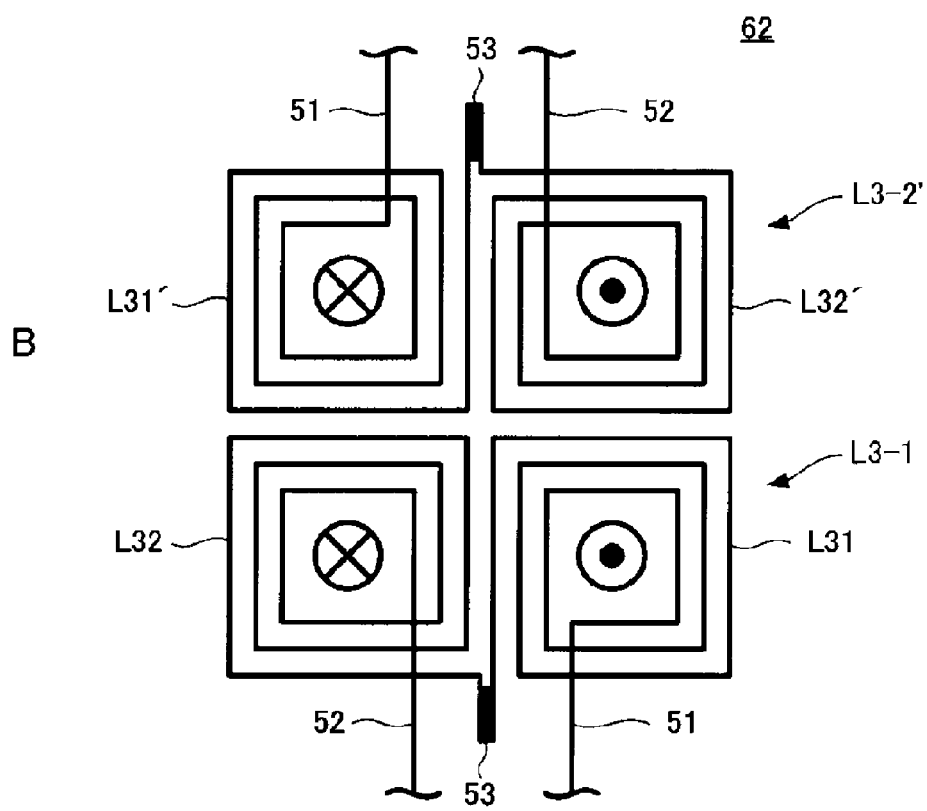

Although the foregoing first through third embodiments (including the first through third modification examples) are described for the case of providing one detector coil, an embodiment of the present disclosure is not limited to such a case, and may also be configured such that two or more detector coils (magnetic coupling elements) are multiply provided, as illustrated in FIG. 16, for example. Correspondingly, the foreign matter detecting apparatus 31 may also be multiply provided. Alternatively, it may be configured such that one or multiple foreign matter detecting apparatus are able to switch among multiply disposed detector coils.

FIG. 16 is an explanatory diagram of a detector coil unit 61 in which two figure 8-shaped detector coils are disposed according to the fourth modification of the first through third embodiments of the present disclosure. FIG. 16A is a plan view illustrating the first example, while FIG. 16B is a plan view illustrating the second example.

In the detector coil unit 61 in the first example of the fourth modification, two detector coils L3-1 and L3-2 are disposed adjacent to each other on the sides which are opposite the sides having their respective leads 51 and 52. The detector coils L3-1 and L3-2 each have a configuration similar to the detector coil L3', with a single detector coil including two spiral-shaped coils. However, the detector coil unit 61 in this example obviously may also be configured using the detector coil L3.

Herein, the respective conductive lines of the detector coil L3-1 and the detector coil L3-2 may also be disposed overlapping by a given amount. By disposing the detector coil L3-1 and the detector coil L3-2 in this way, their detection ranges overlap, which resolves the problem of a dead zone between the detector coil L3-1 and the detector coil L3-2 where foreign matter is not detected.

In the detector coil unit 62 in the second example of the fourth modification, two detector coils L3-1 and L3-2' are disposed adjacent to each other on the sides which are opposite the sides having their respective leads 51 and 52. The coil L31' and the coil L32' of the detector coil L3-2' have a magnetic flux (magnetic field lines) orientation that is the reverse of the coil L31 and the coil L32 of the detector coil L3-2.

Meanwhile, in the multiple detector coils illustrated in FIGS. 16A and 16B, it is desirable for at least one or more coils from among the multiple coils constituting each detector coil to have an inner dimension that is smaller than the inner dimension of the transmitter coil or the receiver coil.

In addition, it is desirable for the overall inner dimension of the multiple coils constituting the multiple detector coils to be smaller than the inner dimension of the transmitter coil or the receiver coil.

Furthermore, it is particularly desirable for the overall outer dimension of the multiple detector coils to be smaller than the inner dimension of the transmitter coil or the receiver coil.

The above is for decreasing change in the electrical properties (such as the Q factor and L value) of the detector coil due to external factors.

Also, in order to effectively suppress unwanted noise produced in the multiple detector coils, it is desirable for the multiple detector coils to be disposed so as to form an approximately symmetrical shape, such as by having approximate rotational symmetry, approximate line symmetry, or approximate point symmetry. However, the configuration is not limited thereto in the case where it is desirable to extend the foreign metal detection range even if the foreign metal detection accuracy drops.

According to the fourth modification of the first through third embodiments discussed above, a single foreign matter detecting apparatus is provided with respect to a detector coil unit having multiple detector coils (magnetic coupling elements), such that multiple detector coils may be used by switching among them in a time division. Also, multiple foreign matter detecting apparatus may be provided such that one of the multiple detector coils may be used as a main detector coil while using the remaining detector coils as auxiliary detector coils.

Note that in the case where the outer dimension across one or multiple detector coils made up of multiple coils is greater than the inner dimension of the receiver coil (or the transmitter coil), it may be difficult to dispose part or all of the one or multiple detector coils in the same plane as the receiver coil (or the transmitter coil). In such cases, it is anticipated that a magnetic or other material may be disposed between all or at least part of the one or multiple detector coils and the receiver coil (or the transmitter coil). This is in order to mitigate drops in the Q factor of the one or multiple detector coils in the case where the one or multiple detector coils are disposed on top of the winding part or the pattern part of the receiver coil (or the transmitter coil).

Fifth Embodiment

Next, an example in which a receiver coil and multiple detector coils (magnetic coupling elements) are disposed outside the same plane will be described as a fifth modification of the first through third embodiments of the present disclosure.

Figure 17:
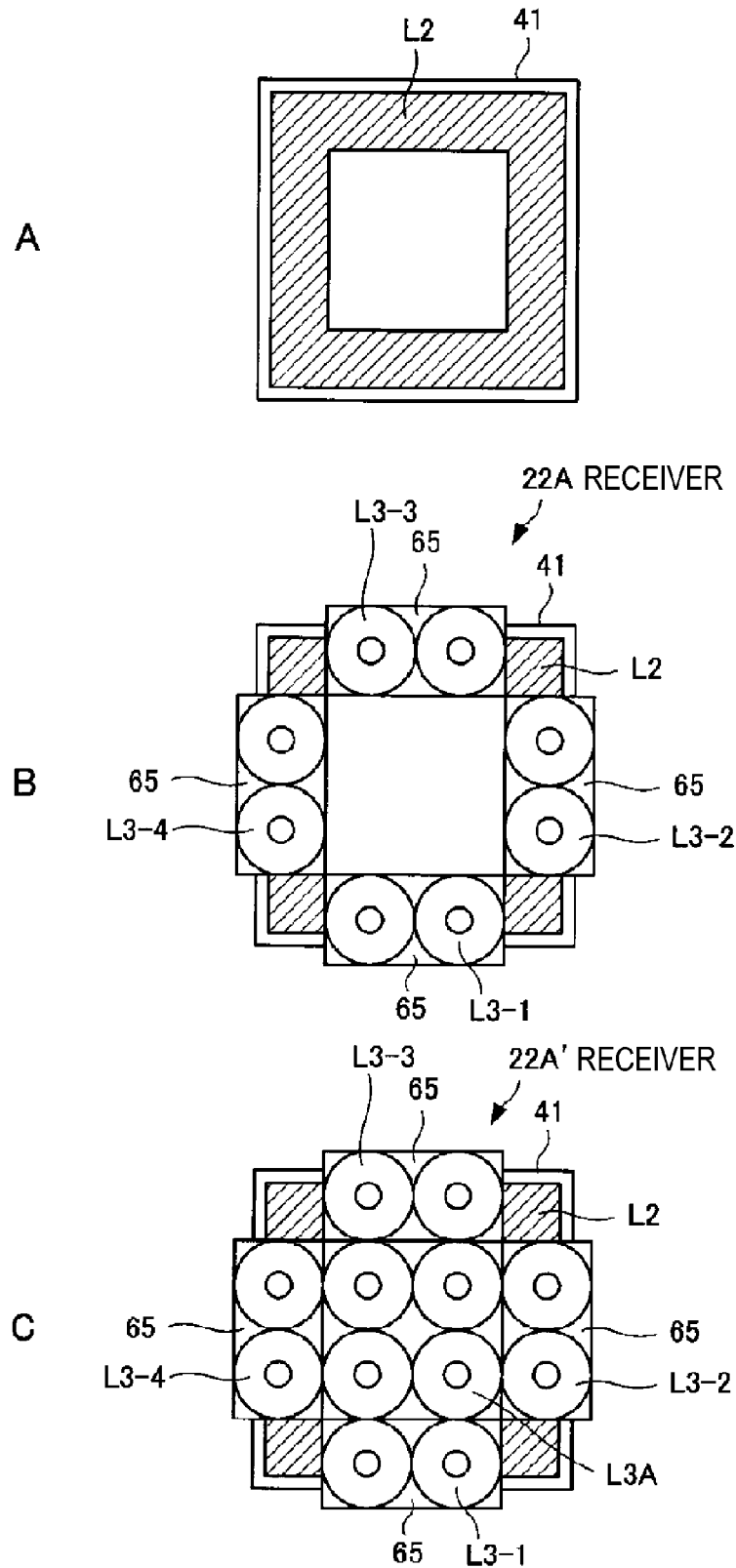
FIG. 17 is an explanatory diagram for exemplary detector coil arrangements according to a fifth modification of the first through third embodiments of the present disclosure, where

FIG. 17 is an explanatory diagram for an exemplary detector coil arrangement according to the fifth modification of the first through third embodiments of the present disclosure. FIGS. 17A, 17B, and 17C are plan views illustrating an example of a receiver coil, an example in which multiple detector coils are disposed on top of the receiver coil, and an example in which some detector coils are disposed in the center of the receiver coil, respectively.

In the receiver 22A illustrated in FIG. 17A, a receiver coil L2 is disposed on top of magnetic shielding material 41, with detector coils L3-1 to L3-4, for example, disposed on top of the receiver coil L2 via magnetic material 65.

The receiver coil L2 is formed by multiply winding conductive wire in a spiral shape (such as an approximately circular shape, an approximately elliptical shape, or an approximately rectangular shape) in the same plane. In this example, conductive wire is wound in an approximately square spiral. Along each of the four edges of the approximately square receiver coil L2, there is placed magnetic material 65 of approximately the same size as the horizontal and vertical Feret diameters (projection widths) of the detector coils L3-1 to L3-4. Additionally, the detector coils L3-1 to L3-4 are disposed on top of the respective magnetic material 65.

The detector coils L3-1 to L3-4 may be four continuously connected figure 8-shaped coils, or split into multiple detector coils, as illustrated in FIGS. 14 to 16B.

Experiment has confirmed that foreign metal may be detected with the foregoing fifth modification of the first through third embodiments described above, similarly to the first through fourth embodiments (including the first through fourth modification examples), even in the case where the receiver coil and the detector coil are disposed outside the same plane, or in other words, even when not disposed on the same plane in the Z direction.

Note that although it is desirable to dispose magnetic material between the receiver coil L2 and the detector coils L3-1 to L3-4 as illustrated in FIG. 17B in order to mitigate drops in the Q factor of the detector coils, the configuration is not limited thereto.

In addition, a receiver 22A' may also be configured by disposing detector coils in the center of the receiver coil L2, as illustrated in FIG. 17C. In this case, it is also conceivable to dispose some of the detector coils (such as the detector coils L3A in FIG. 17C, for example) in the same plane as the receiver coil L2, while disposing the remaining detector coils outside the same plane as the receiver coil L2. Obviously, all detector coils may also be disposed outside the same plane as the receiver coil L2.

Sixth Embodiment

Next, exemplary countermeasures for the case where foreign metal generates heat over a wide range will be described as the sixth modification of the first through third embodiments of the present disclosure.

Figure 18:
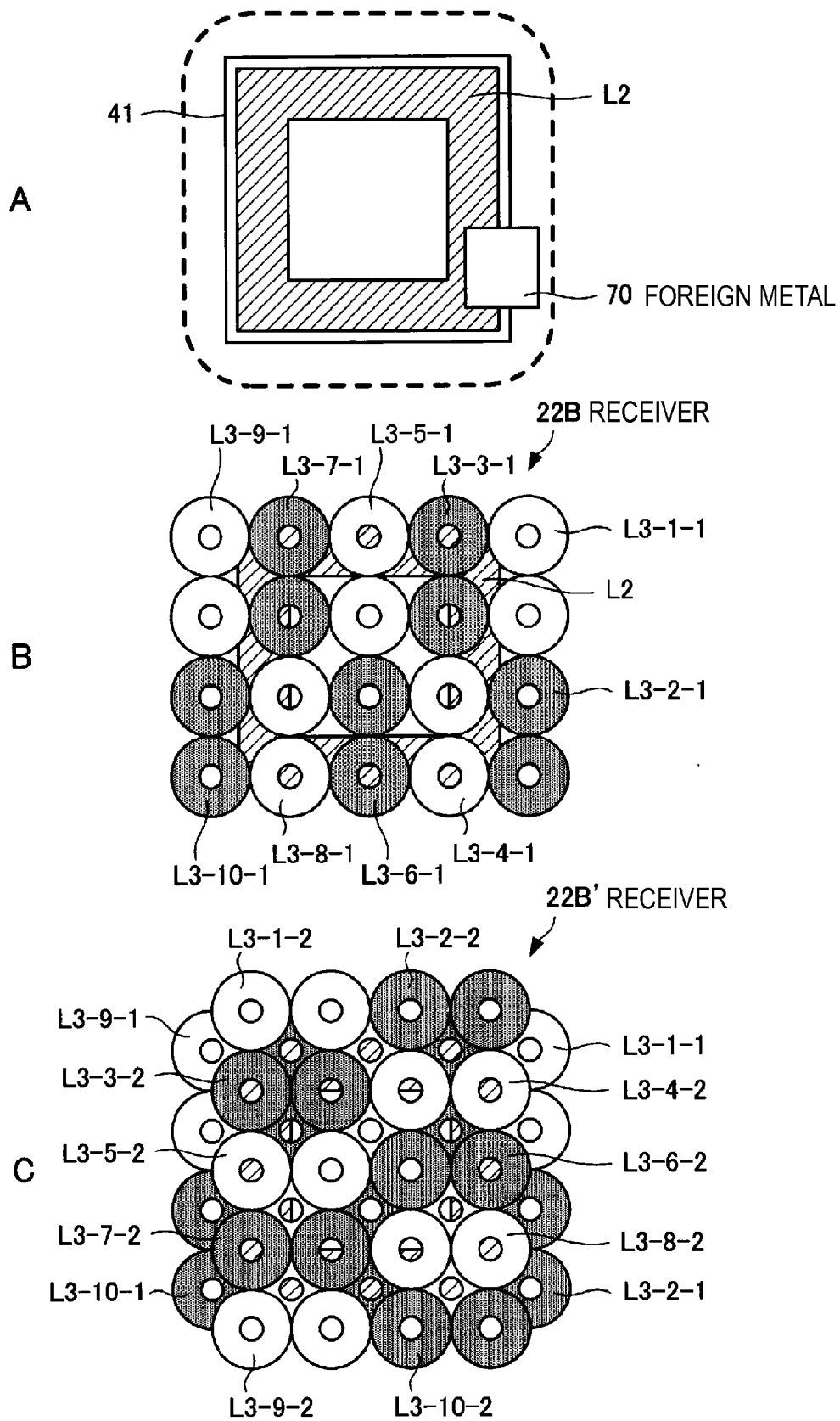
FIG. 18 is an explanatory diagram for exemplary detector coil arrangements according to a sixth modification of the first through third embodiments of the present disclosure, where

FIG. 18 is an explanatory diagram for an exemplary detector coil (magnetic coupling element) arrangement according to the sixth modification of the first through third embodiments of the present disclosure. FIGS. 18A, 18B, and 18C are plan views illustrating an example of a receiver coil and foreign metal, an example in which multiple detector coils are disposed on top of the receiver coil, and an example in which multiple detector coils are additionally disposed on top of the multiple detector coils in FIG. 18B, respectively.

As illustrated in FIG. 18A, it is conceivable that foreign metal 70 may generate heat over a wide area on the outside of the receiver coil L2 (the area enclosed by broken lines). In cases where foreign metal generates heat over a wide area in this way, it is conceivable to dispose multiple detector coils over a wide area as a countermeasure.

In the receiver 22B illustrated in FIG. 18B, 10 figure 8-shaped detector coils L3-1-1 to L3-10-1, for example, are disposed on top of the receiver coil L2. The overall horizontal and vertical Feret diameters of these 10 detector coils are greater than the receiver coil L2. In FIG. 18B, the detector coils are alternately shaded and unshaded in order to distinguish between adjacent figure 8-shaped detector coils.

However, in the case of the exemplary arrangement in FIG. 18B, a dead zone where foreign metal is not detected may exist between a given detector coil and an adjacent detector coil. For this reason, in some cases it may also be desirable to dispose detector coils in two or more layers, like in the exemplary arrangement in FIG. 18C. Herein, a receiver 22B' is configured by disposing 10 detector coils L3-1-1 to L3-10-1 (the first layer) on top of the receiver coil L2, and additionally disposing 10 more detector coils L3-1-2 to L3-10-2 (the second layer) on top of the first layer.

At this point, the problem of a dead zone between adjacent detector coils may be resolved by disposing the second layer of detector coils shifted by ½ pitch with respect to the first layer of detector coils. Also, if the figure 8-shaped detector coils in the first layer are arranged vertically (in the Y direction) and the detector coils in the second layer are arranged horizontally (in the X direction), it is possible to detect magnetic flux changes in a different direction than the first layer of detector coils, thus reliably resolving the dead zone problem and improving foreign metal detection accuracy.

According to the foregoing sixth modification of the first through third embodiments, it is possible to detect foreign metal over a wide range of the receiver coil. Also, by disposing the detector coils in two or more layers, it becomes possible to resolve the problem of dead zones where foreign metal is not detected.

Modification 7

Figure 19:
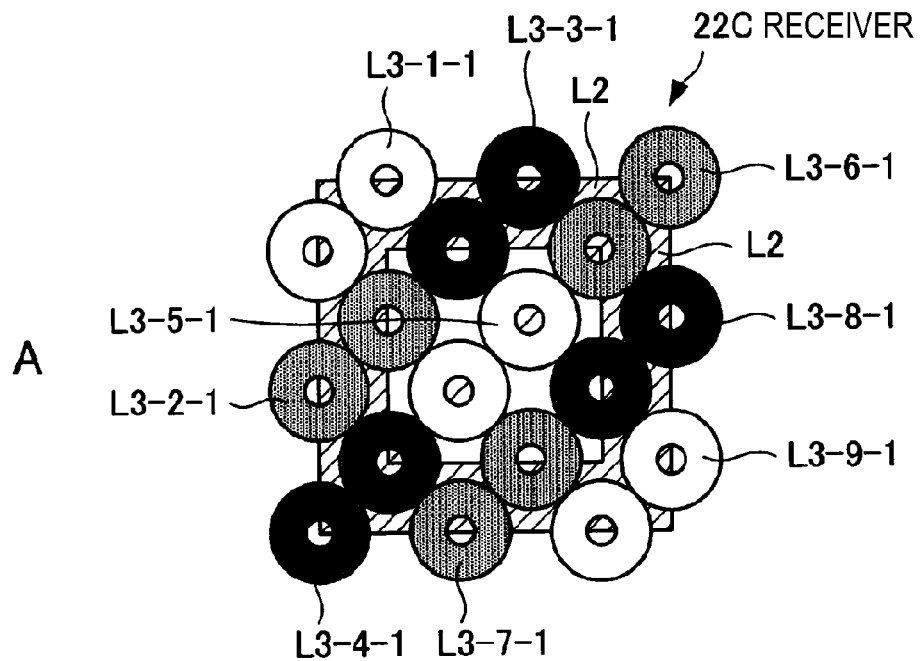
FIG. 19 is an explanatory diagram for exemplary detector coil arrangements according to a seventh modification of the first through third embodiments of the present disclosure, where
Figure 19:
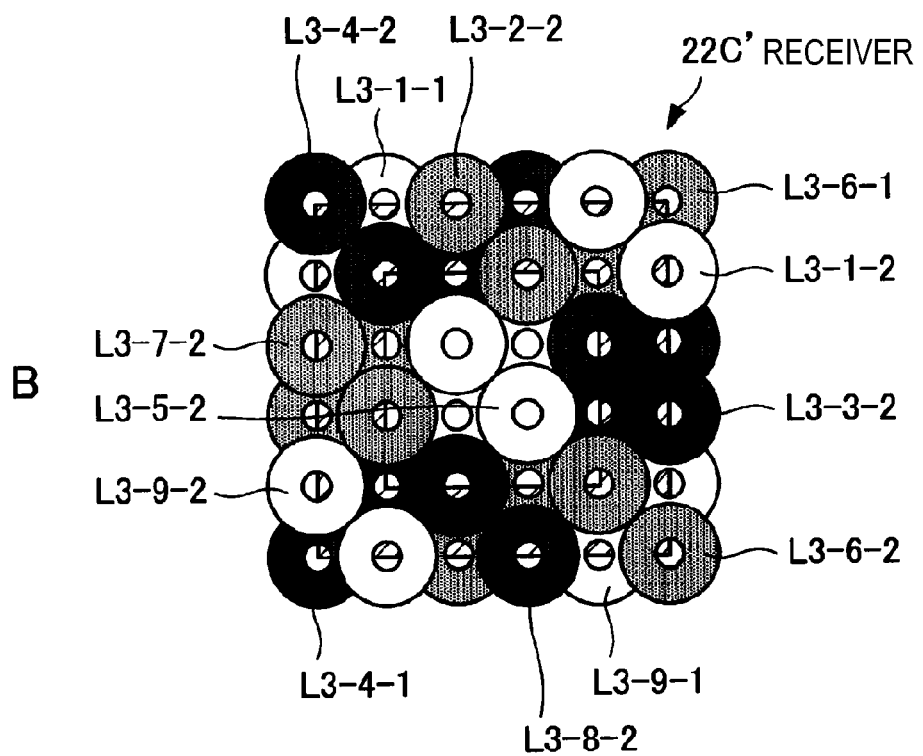

FIG. 19 is an explanatory diagram for exemplary detector coil arrangements according to a seventh modification of the first through third embodiments of the present disclosure. FIGS. 19A and 19B are plan views illustrating an example in which multiple detector coils are disposed on top of the receiver coil, and an example in which multiple detector coils are additionally disposed on top of the multiple detector coils in FIG. 19A, respectively.

Whereas detector coils are disposed in the horizontal and vertical directions of the receiver 22B according to the sixth embodiment illustrated in FIG. 18, detector coils are disposed in the diagonal direction of the receiver coil in the example illustrated in FIG. 19.

In the receiver 22C illustrated in FIG. 19B, nine figure 8-shaped detector coils L3-1-1 to L3-9-1, for example, are disposed on top of the receiver coil L2 in the diagonal direction of the approximately square receiver coil L2. The overall horizontal and vertical Feret diameters of these nine detector coils are greater than the receiver coil L2. In FIG. 19B, the detector coils are alternately unshaded, shaded gray, and shaded black in order to distinguish between adjacent figure 8-shaped detector coils.

Also, in order to resolve the problem of a dead zone between adjacent detector coils, a receiver 22C' is configured by disposing a first layer of detector coils L3-1-1 to L3-9-1 on top of the receiver coil L2, and disposing a second layer of detector coils L3-1-2 to L3-9-2 on top of the first layer. At this point, the second layer of detector coils L3-1-2 to L3-9-2 are disposed in a different diagonal direction than that of the first layer of detector coils L3-1-1 to L3-9-1.

According to this example, a second layer of detector coils is disposed in a different diagonal direction that that of the first layer of detector coils, thereby making it possible to detect magnetic flux changes in a different direction than the first layer of detector coils, and thus reliably resolving the dead zone problem and improving foreign metal detection accuracy.

5. Fourth Embodiment

A magnetic coupling element (detector coil) used in the first through third embodiments discussed above is shaped like multiple coils electrically connected together, in which the magnetic flux produced from at least one or more of these multiple coils and the magnetic flux produced from the remaining of these multiple coils have approximately opposing orientations.

However, if properties such as the L values, R values, and Q factors of the individual coils constituting one or multiple such magnetic coupling elements differ greatly from each (exhibit variance), the problem of greatly differing foreign matter detection accuracies may occur depending on the relative position of the detector coil and the foreign matter.

If the individual electrical properties of multiple coils differ greatly, there is a risk of excessive voltage being produced in a magnetic coupling element due to the magnetic flux used in a contactless power supply system, for example. Since such excessive voltage may lead to error when measuring electrical properties (electrical parameters) related to a magnetic coupling element, excessive voltage may become a factor that worsens foreign matter detection accuracy.

Also, in cases where excessive voltage may be produced, it is desirable to design the circuit portions electrically connected to a magnetic coupling element to have a high withstanding voltage, which may lead to increases in the dimensions (size) of the circuit portions and in component costs.

Figure 20:
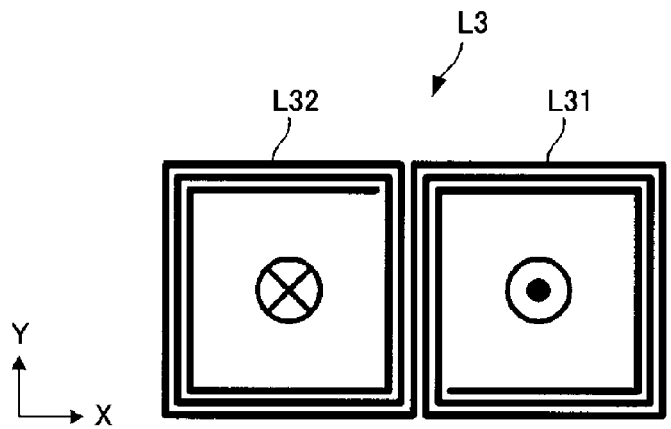
FIG. 20 is a plan view illustrating a detector coil in a state where positioning units are not disposed.

This point will now be described with reference to FIG. 20. FIG. 20 is a plan view illustrating a detector coil L3 in a state where positioning units are not disposed. The detector coil L3 has a basic configuration of a magnetic coupling element including two coils L31 and L32.

In this detector coil L3, the coil L31 and the coil L32 are electrically connected (joined) such that the magnetic flux (magnetic field lines) produced from the coil L31 and the coil L32 have approximately opposing orientations (see FIG. 8). In the case of detecting foreign matter using such a detector coil, it is desirable for the two coils L31 and L32 to have approximately the same shapes and dimensions. Realistically, however, the shapes and dimensions of the two coils L31 and L32 may differ, particularly in the case of realizing the detector coil L3 with winding wire. As a result, electrical properties such as the coil L value, R value, and Q factor may differ between two coils L31 and L32.

Figure 21:
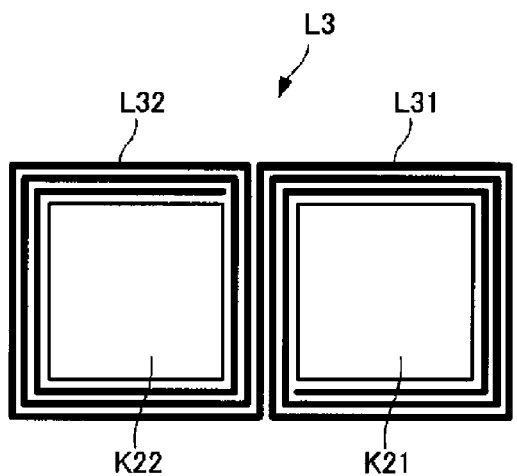
FIG. 21 is an explanatory diagram according to an example of the fourth embodiment of the present disclosure, and is a plan view illustrating an example of the case of disposing two positioning units.
Figure 22:
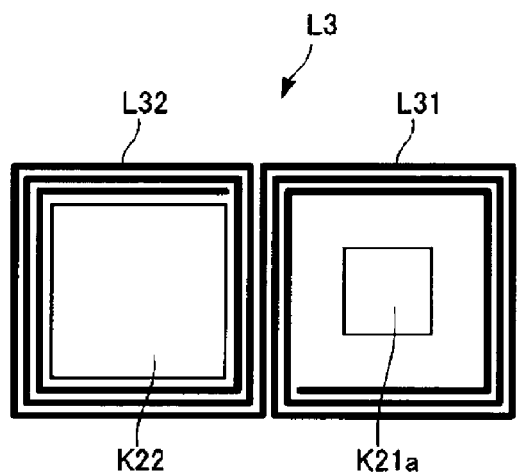
FIG. 22 is an explanatory diagram according to another example of the fourth embodiment of the present disclosure, and is a plan view illustrating an example of the case of modifying the size of either one of two positioning units.
Figure 23:
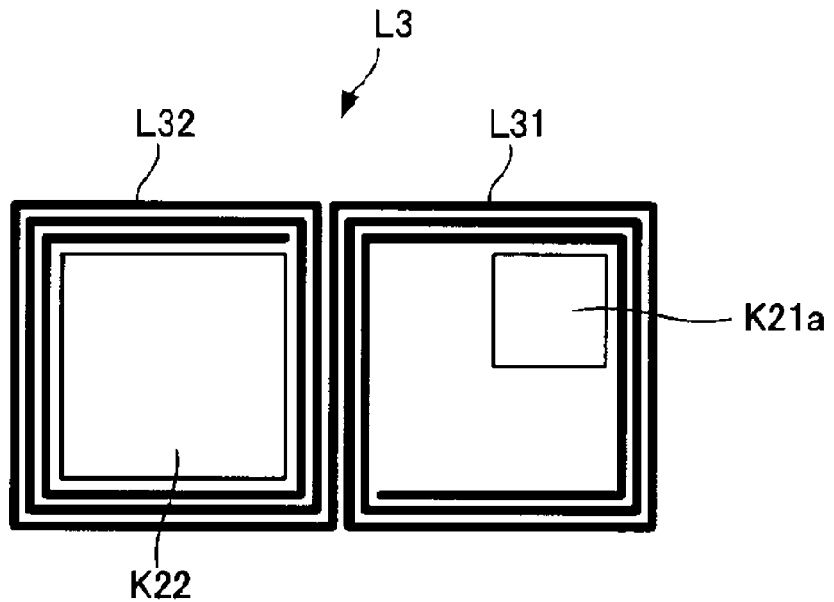
FIG. 23 is an explanatory diagram according to another example of the fourth embodiment of the present disclosure, and is a plan view illustrating an example of the case of modifying the position of either one of two positioning units.

Thus, differing electrical properties such as the L value, R value, and Q factors among multiple coils is counteracted by using magnetic material to realize positioning units disposed on the inner side of at least one coil from among the multiple coils constituting one or multiple detector coils. Herein, FIGS. 21 to 23 are exemplary plan view configurations (exemplary X-Y plan view configurations) illustrating examples of such, in which positioning units K21 and K22 realized with magnetic material are disposed on the respective inner sides of two coils (L31 and L32) constituting the detector coil L3. In the description hereinafter, the positioning units K21 and K22 may also be collectively designated the positioning unit K2.

First, FIG. 21 is an explanatory diagram according to an example of the fourth embodiment of the present disclosure, and is a plan view illustrating an example of the case of disposing two positioning units.

This example is for the case of making the coil L31 and the coil L32 have approximately the same coil electrical properties (electrical parameters) by differentiating the positioning units K21 and K22 from each other with factors such as the effective permeability (the real part $\mu'$ of the permeability) and hysteresis loss (the imaginary part $\mu''$ of the permeability), the outermost dimension in the Z direction (thickness), and the placement in the Z direction of the magnetic material. In other words, the two positioning units K21 and K22 have the same shape and placement as viewed from above.

Next, FIG. 22 is an explanatory diagram according to another example of the fourth embodiment of the present disclosure, and is a plan view illustrating an example of the case of modifying the size of either one of two positioning units.

This example is for the case of making the coil L31 and the coil L32 have approximately the same coil electrical properties (electrical parameters) by differentiating a positioning unit K21a and a positioning unit K22 from each other with factors such as the effective permeability (the real part $\mu'$ of the permeability) and hysteresis loss (the imaginary part $\mu''$ of the permeability), the outermost dimension in the Z direction (thickness), and the placement in the Z direction of the magnetic material discussed above, in addition to the outermost dimension (size) of the magnetic material in the X and Y directions.

FIG. 23 is an explanatory diagram according to another example of the fourth embodiment of the present disclosure, and is a plan view illustrating an example of the case of modifying the position of either one of two positioning units.

This example is for the case of making the coil L31 and the coil L32 have approximately the same coil electrical properties (electrical parameters) by differentiating the positioning unit K21a and the positioning unit K22 from each other with factors such as the effective permeability (the real part $\mu'$ of the permeability) and hysteresis loss (the imaginary part $\mu''$ of the permeability), the outermost dimension in the Z direction (thickness), the placement in the Z direction, and the outermost dimension (size) in the X and Y directions of the magnetic material, in addition to the placement of the positioning unit K2 in the X and Y directions.

Figure 24:
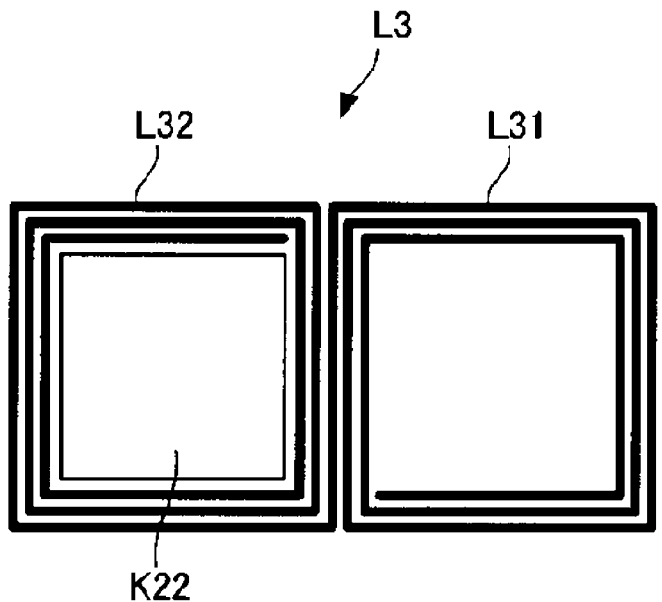
FIG. 24 is an explanatory diagram according to another example of the fourth embodiment of the present disclosure, and is a plan view illustrating an example of the case of not disposing one of two positioning units.

FIG. 24 is an explanatory diagram according to another example of the fourth embodiment of the present disclosure, and is a plan view illustrating an example of the case of not disposing one of two positioning units.

This example is for the case of making the coil L31 and the coil L32 have approximately the same coil electrical properties (electrical parameters) by disposing a positioning unit K2 (in this example, the positioning unit K22) on the inner side of only one coil from between the coil L31 and the coil L32.

Note that although examples of the case of disposing one each of a positioning unit K21 (K21a) and a positioning unit K22 are described with the above FIGS. 21 to 24, the configuration is not limited to such examples. Two or more of the same positioning units K2 (multiple positioning units K2) may also be disposed, and two or more (multiple) types differentiated by their effective permeability (the real part $\mu'$ of the permeability), hysteresis loss (the imaginary part $\mu''$ of the permeability), outermost dimensions (size) in the X, Y, and Z directions, and placement in the X, Y, and Z directions may also be disposed.

Also, although the description of the above FIGS. 21 to 24 used the case where the outermost dimension of a positioning unit K2 is smaller than the innermost dimension of the coil L31 or L32 as an example, the case of being larger than the innermost dimension of the coil L31 or L32 is also anticipated (see FIG. 12, for example). Furthermore, the case where the outermost dimension of a positioning unit K2 is smaller than the outermost dimension of the coil L31 or L32 is also anticipated.

However, since these cases involve ensuring space for the thickness of the positioning units K2 and thickness of an anchoring material for anchoring the placement of the detector coil L3 and the positioning unit K2, in addition to the thickness of the detector coil L3, it is often desirable for the outermost dimension of a positioning unit K2 to be smaller than the innermost dimension of the coil L31 or L32.

Herein, the effective permeability (the real part $\mu'$ of the permeability) of a positioning unit K2 primarily affects the L value of the detector coil, the hysteresis loss (the imaginary part $\mu''$ of the permeability) of a positioning unit K2 primarily affects the R value of the detector coil, while the outermost dimensions (size) in the X, Y, and Z directions and the placement or thickness in the X, Y, and Z directions (in other words, the quantity or number of units to dispose) affects the L value and the R value of the detector coil.

Also, as mentioned in the description of the first embodiment, since there is a larger increase in the L value than in the R value of the detector coil in the case where the hysteresis loss (the imaginary part $\mu''$ of the permeability) of the positioning units K2 is extremely small and the effective permeability (the real part $\mu'$ of the permeability) of the magnetic material is large, it becomes possible to improve the Q factor of the detector coil. For this reason, it is desirable that the magnetic material used for the positioning units K2 cause a greater increase in the L value of the detector coil than the R value.

In other words, it is desirable to use positioning units K2 that establish a relationship of $\mu' > \mu''$, particularly $\mu' \gg \mu''$, between the real part $\mu'$ and the imaginary part $\mu''$ of the permeability of the magnetic material. However, the configuration is not limited thereto if dropping the Q factor of the detector coil is not problematic.

By changing the specifications and layout of the positioning units K2 in this way, it becomes possible to make the electrical properties (such as the L value, R value, and Q factor) of the two coils L31 and L32 constituting the detector coil L3 approximately the same. Potential examples of the specifications and layout of the positioning units K2 include the effective permeability (the real part µ' of the permeability), the hysteresis loss (the imaginary part µ" of the permeability), the outermost dimensions (size) in the X, Y, and Z directions, the placement in the X, Y, and Z directions, and the quantity (number) of units to dispose, for example.

In the examples of the present embodiment discussed above, there is described an example of making the electrical properties (electrical parameters) of two coils L31 and L32 approximately the same by utilizing positioning units K2 made of magnetic material disposed in the two coils L31 and L32. However, it may also be configured such that the electrical properties (electrical parameters) of three or more coils are made approximately the same by appropriately changing factors such as the specifications and layout of positioning units, and disposing the positioning units with respect to three or more coils constituting a magnetic coupling element.

Next, the results of measuring the electrical properties (electrical parameters) of coils constituting a detector coil will be described.

The detector coil L3' illustrated in FIG. 13 is an example of a detector coil realized by electrically connecting two coils L31 and L32 in which wire is wound a given number of times. In such a case, the electrical properties of the coil L31 are measurable with the combination of a junction 53 (terminal T1) and a lead 51 (terminal T2A), while the electrical properties of the coil L32 are measurable with the combination of the junction 53 (terminal T1) and a lead 52 (terminal T2B).

Figure 25:
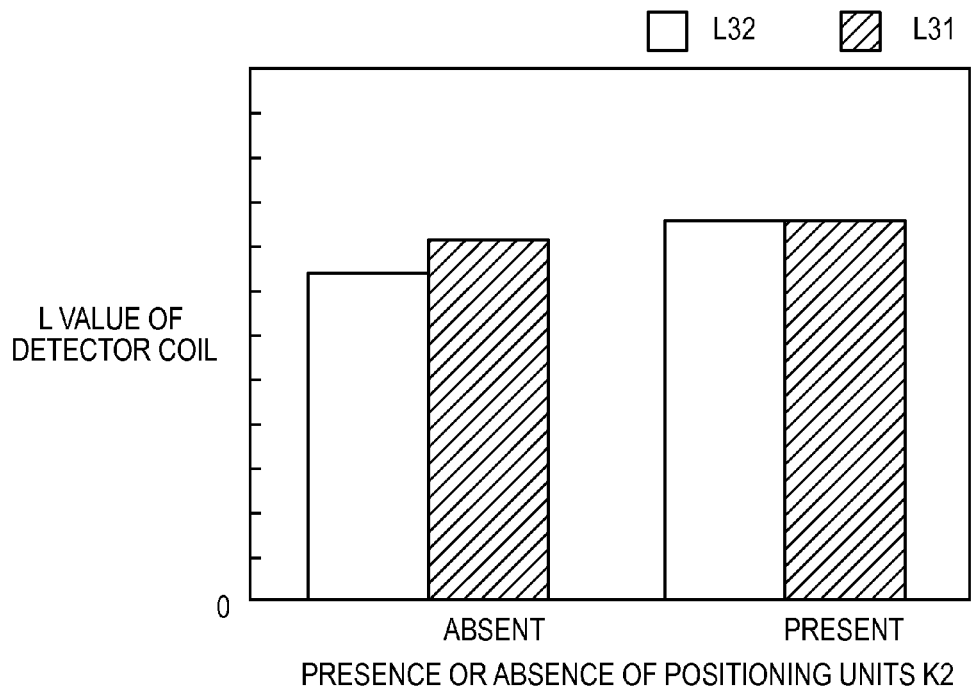
FIG. 25 is a graph illustrating an example of the difference in the L value of a detector coil according to whether or not positioning units are present.
Figure 26:
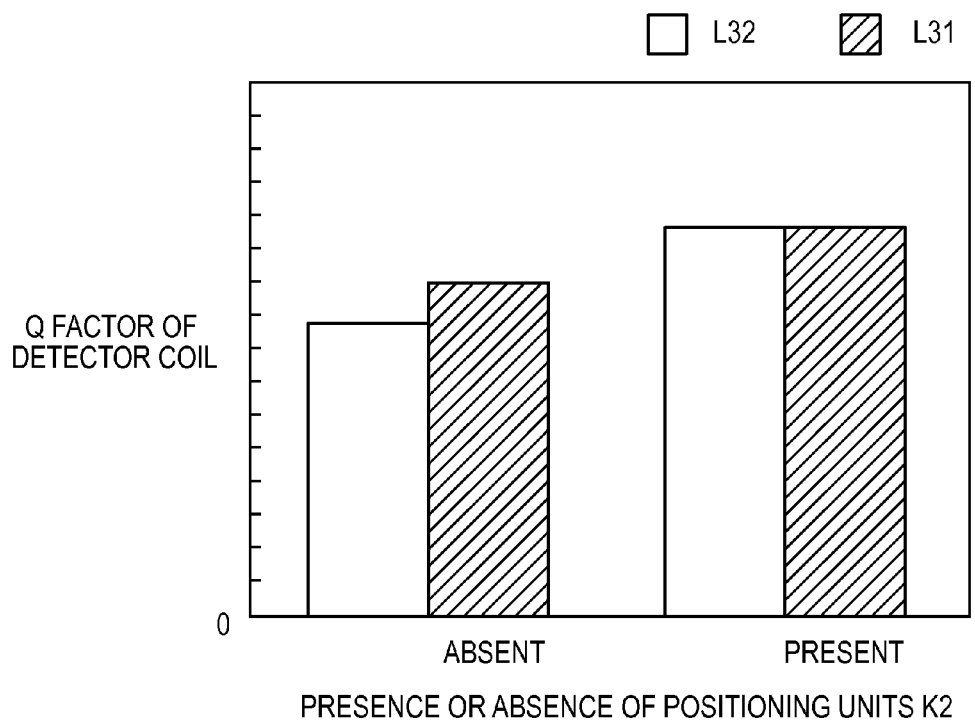
FIG. 26 is a graph illustrating an example of the difference in the Q factor of a detector coil according to whether or not positioning units are present.

FIG. 25 is a graph illustrating an example of the difference in the L value of the detector coil L3' according to whether or not positioning units are present. FIG. 26 is a graph illustrating an example of the difference in the Q factor of the detector coil L3' according to whether or not positioning units are present.

FIG. 25 (left side) and FIG. 26 (left side) respectively illustrate the L value and the Q factor in the case where the electrical properties of the coil L31 and the coil L32 differ from each other. FIG. 25 (right side) and FIG. 26 (right side) respectively illustrate the L value and the Q factor in the case of utilizing positioning units K2 to make the electrical properties of the coil L31 and the coil L32 approximately the same.

As illustrated in FIGS. 25 and 26, it is possible to improve the L value and Q factor of the coil L31 and the coil L32 by utilizing positioning units K2. FIGS. 25 and 26 also demonstrate that it is possible to adjust the electrical properties so as to make the L value and the Q factor approximately the same between the coil L31 and the coil L32. Note that, according to the formula related to the Q factor discussed earlier, the R value is also adjusted to be approximately the same in this case.

Figure 27:
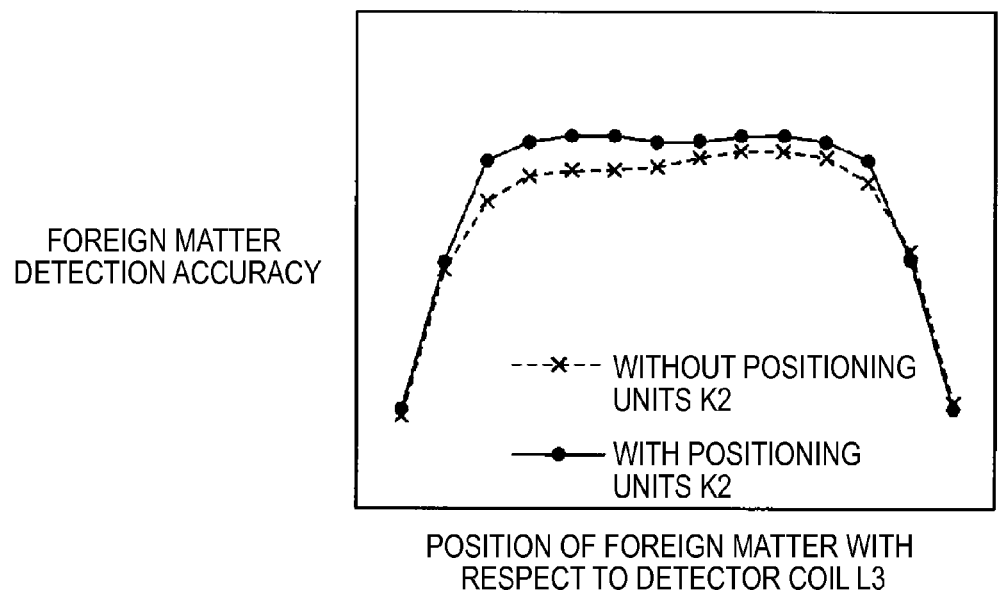
FIG. 27 is a graph illustrating an exemplary relationship between the position of foreign matter with respect to a detector coil, and the foreign matter detection accuracy.

FIG. 27 is a graph illustrating how much the foreign matter detection accuracy changes depending on whether or not positioning units K2 are present, according to the relative placement of the detector coil L3 and foreign matter.

On the horizontal axis in FIG. 27, the central portion corresponds to positions above the detector coil, while the sides of the central portion correspond to positions distanced from above the detector coil. FIG. 27 demonstrates that in the case of utilizing positioning units K2 to adjust the L value and Q factor of the coil L31 and the coil L32, foreign matter detection accuracy is approximately uniform even if foreign matter is disposed over a wide range with respect to the detector coil L3.

At this point, consider the case of disposing magnetic shielding material 41, a receiver coil L2, a detector coil L3, as well as positioning units K21 and K22 inside a secondary device (electronic device) of the contactless power supply system 100, as illustrated in FIG. 6B.

Figure 28:
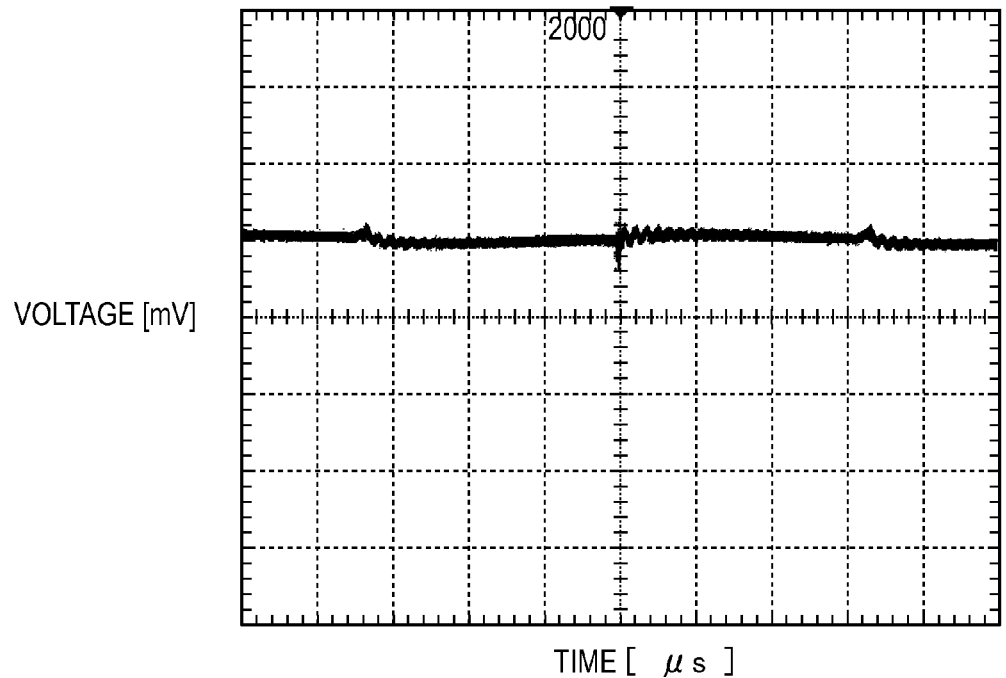
FIG. 28 is a waveform diagram illustrating an example of a waveform of voltage (voltage waveform) produced in an LC resonator including a detector coil and a resonant capacitor, in the case where there is a small difference in the electrical properties between the two coils constituting the detector coil.
Figure 29:
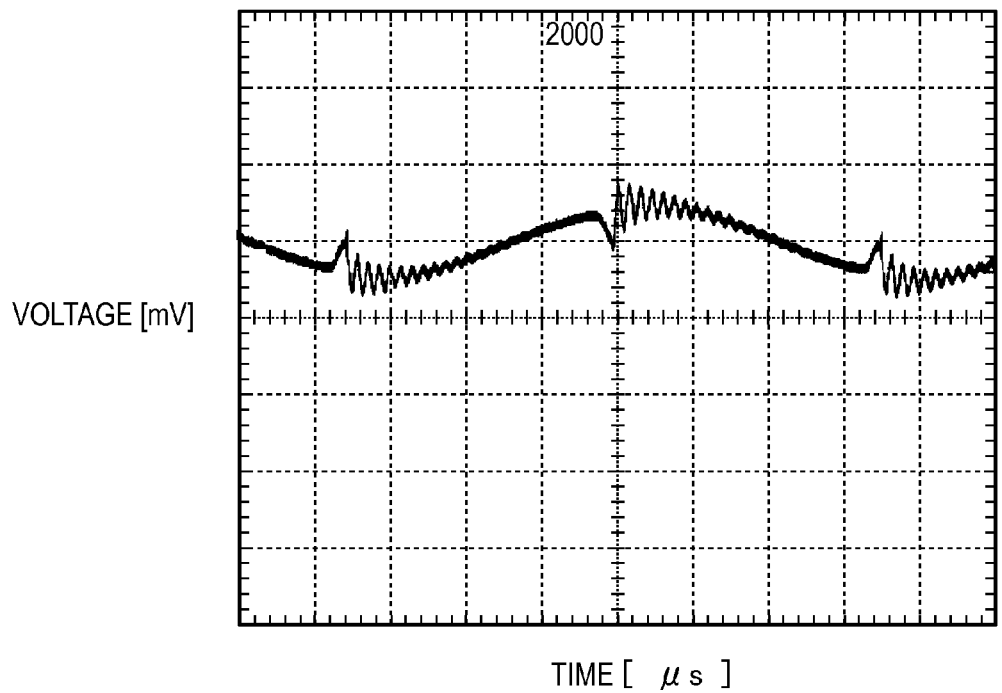
FIG. 29 is a waveform diagram illustrating an example of a waveform of voltage (voltage waveform) produced in an LC resonator including a detector coil and a resonant capacitor, in the case where there is a large difference in the electrical properties between the two coils constituting the detector coil.
Figure 30:
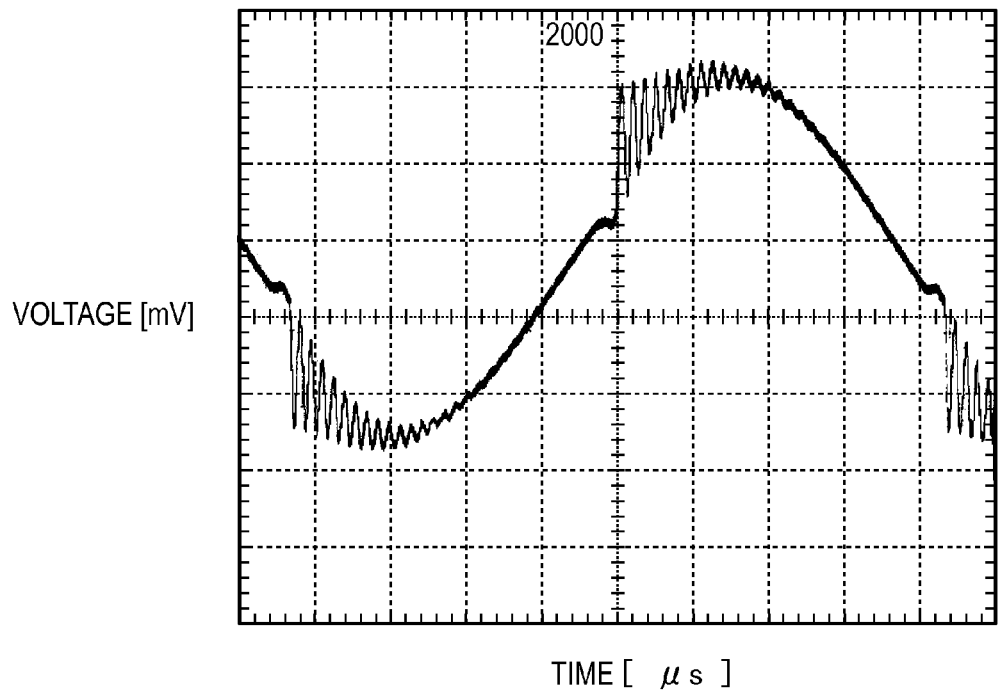
FIG. 30 is a waveform diagram illustrating an example of a waveform of voltage (voltage waveform) produced in an LC resonator including a detector coil and a resonant capacitor, in the case where there is a very large difference in the electrical properties between the two coils constituting the detector coil.

FIGS. 28 to 30 illustrate exemplary waveforms of voltage produced in the detector coil L3 upon receiving magnetic flux (magnetic field lines; a magnetic field) produced from the transmitter coil L1 or the receiver coil L2 during contactless power supply by the contactless power supply system 100. A voltage corresponding to the difference in the electrical properties (such as the L value, R value, and Q factor) between the coil L31 and the coil L32 is produced in the detector coil L3.

FIG. 28 illustrates an example for the case of a small difference in the electrical properties between the coil L31 and the coil L32, and demonstrates that negligible voltage is produced in the detector coil L3 in this case. The voltage measured in this example has an effective value of 27.7 mV, and a peak-to-peak (p-p) value of 390 mV.

FIG. 29 illustrates an example for the case of a large difference in the electrical properties between the coil L31 and the coil L32, and demonstrates that a large voltage is produced in the detector coil L3 in this case. The voltage measured in this example has an effective value of 169 mV, and a p-p value of 750 mV.

FIG. 30 illustrates an example for the case of an extremely large difference in the electrical properties between the coil L31 and the coil L32, and demonstrates that an extremely large voltage is produced in the detector coil L3 in this case. The voltage measured in this example has an effective value of 832 mV, and a p-p value of 2.56 mV.

As these measurement results indicate, a large voltage is produced in the detector coil L3 if there is a large difference in electrical properties (electrical parameters) between the coil L31 and the coil L32. This voltage becomes noise when detecting foreign matter, and may become a factor that lowers the foreign matter detection accuracy.

Action and Advantages of Fourth Embodiment

According to the fourth embodiment described above, action and advantages like the following are obtained.

For example, if the fourth embodiment is applied to a foreign matter detection system using a magnetic coupling element, it is possible to realize an approximately uniform detection accuracy with respect to foreign matter within a given area where foreign matter present in a contactless power supply or other system may generate heat, irrespective of the relative positions of the magnetic coupling element and the foreign matter.

Also, the fourth embodiment prevents the production of excessive voltage in a magnetic coupling element of a foreign matter detection system due to magnetic flux used in a contactless power supply or other system. Thus, there is decreased error when measuring electrical properties (electrical parameters) related to a detector coil, and reduced worsening of the foreign matter detection accuracy.

Furthermore, it is also possible to improve the foreign matter detection accuracy in a foreign matter detection system that detects the presence of foreign metal on the basis of changes in the Q factor of an LC resonator (resonant circuit) that at least includes a magnetic coupling element, or of the magnetic coupling element itself.

Note that in a contactless power supply system that aligns a primary device and a secondary device by using a magnet disposed inside either the primary device or the secondary device, and magnetic material disposed inside the other device, it is possible to use the magnetic material utilized in the present embodiment (such as for the positioning units K2, for example) jointly as the magnetic material for such alignment.

The foregoing thus describes, as an example of the fourth embodiment of the present disclosure, an electrical properties adjustment method in which positioning units are disposed on the inner side of a single magnetic coupling element (a figure 8-shaped coil) realized with two coils, and in which the electrical properties (electrical parameters) of the two coils are made approximately the same by varying factors such as their specifications and layout. However, the configuration is not limited to such an example, and an electrical properties adjustment method according to the fourth embodiment may also be applied to one or multiple magnetic coupling elements which may be applied to the first through third embodiments discussed earlier.

Meanwhile, in the foregoing first through third embodiments, it was described that in some cases, in order to further improve foreign matter detection accuracy, for example, it may be more desirable to use one or multiple magnetic coupling elements shaped like multiple coils electrically connected together, in which the magnetic flux produced from at least one or more of these multiple coils and the magnetic flux produced from the remaining of these multiple coils have approximately opposing orientations. However, the configuration is not limited thereto if worsening the foreign matter detection accuracy is not problematic. In other words, cases are also conceivable in which magnetic flux with approximately the same orientation is produced from multiple coils constituting one or multiple magnetic coupling elements to which the fourth embodiment is applied.

Additionally, it becomes possible to make the electrical properties (electrical parameters) of multiple coils constituting one or multiple magnetic coupling elements approximately the same, by varying factors such as the effective permeability (the real part $\mu'$ of the permeability), the hysteresis loss (the imaginary part $\mu''$ of the permeability), the outermost dimensions (size) in the X, Y, and Z directions, the placement in the X, Y, and Z directions, and the quantity (number) of positioning units disposed near at least one or more coils from among the multiple coils constituting the one or multiple magnetic coupling elements.

However, as discussed earlier, although it is particularly desirable to dispose the positioning units in the inner vicinity of at least one or more coils from among the multiple coils constituting the one or multiple magnetic coupling elements, the configuration is not limited thereto.

It may also be configured such that, in correspondence with the first through third embodiments discussed earlier, positioning units provided in the outer vicinity of at least one or more coils from among the above multiple coils are utilized to make the electrical properties (electrical parameters) of the multiple coils approximately the same.

Furthermore, although the foregoing description uses an example of utilizing positioning units to adjust all of the L value, R value, and Q factor of a magnetic coupling element (coil), the configuration is not only limited to such cases, and it is sufficient at adjust at least one or more of the L value, R value, and Q factor of a magnetic coupling element.

Moreover, although the foregoing is described with an example of utilizing positioning units to adjust the L value, R value, and Q factor of a magnetic coupling element, the configuration is not only limited to such cases, and it is also anticipated that adjustment may be made on the basis of some kind of electrical property (electrical parameter) related to a magnetic coupling element.

For example, obviously also anticipated is the case of making adjustments on the basis of some kind of electrical property (electrical parameter) related to a single magnetic coupling element or to an apparatus and system utilizing a magnetic coupling element, such as a power value, a voltage value, a current value, a power factor, an energy efficiency, a power supply efficiency, a charging efficiency, an energy loss, the amplitude, phase, period, pulse width, or duty cycle of a detection signal, an impedance value, a mutual inductance value, a coupling coefficient, a magnetic flux magnitude, a magnetic flux density, a capacitance value, a self-inductance value, a resonant frequency, a carrier wave frequency, a signal wave frequency, a modulation factor, a signal level, a noise level, or a temperature.

6. Other

The foregoing first through fourth embodiments are described for the case of providing a foreign matter detecting apparatus including one or more detector coils in an electronic device given as a secondary device (power recipient device).

However, an embodiment of the present disclosure is not limited to such a case, and may also be configured such that a foreign matter detecting apparatus including one or more detector coils is provided in a power supply apparatus given as a primary device. In such cases, the receiver coil described in the foregoing first embodiment may be substituted with a transmitter coil, and the transmitter coil may be substituted with a receiver coil. A foreign matter detecting apparatus including one or more detector coils may also be disposed in both a primary device and a secondary device.

Furthermore, it may also be configured such that a foreign matter detecting apparatus including one or more detector coils is provided in another apparatus separate from a primary device and a secondary device.

In other words, it may be configured such that the foreign matter detecting apparatus including one or more detector coils described in the foregoing embodiments is provided in at least one of a primary device, a secondary device given as a power recipient device, and another apparatus separate from the primary device and the secondary device.

Also, in the description of the foregoing embodiments, there is described the example of a system (such as a foreign matter detecting apparatus, for example) that detects the presence of foreign matter from change in the Q factor of a magnetic coupling element (detector coil), or from change in the Q factor of an LC resonator (resonant circuit) that at least includes a magnetic coupling element. However, the above system is not limited to such an example, and may also be a foreign matter detection system that detects the presence of foreign matter using a separate technique related to a magnetic coupling element.

For example, a case is also conceivable in which foreign matter is detected on the basis of other electrical properties (electrical parameters) which are calculated (estimated, indirectly measured) on the basis of measurement results for the Q factor of a magnetic coupling element, or measurement results for the Q factor of an LC resonator (resonant circuit) that at least includes a magnetic coupling element.

Also conceivable is a case in which foreign matter is detected on the basis of changes in some kind of electrical property (electrical parameter) related to an individual magnetic coupling element, or to an apparatus and system that utilize a magnetic coupling element. Potential examples of such an electrical property (electrical parameter) include a power value, a voltage value, a current value, a power factor, an energy efficiency, a power supply efficiency, a charging efficiency, an energy loss, the amplitude, phase, period, pulse width, or duty cycle of a detection signal, an impedance value, a mutual inductance value, a coupling coefficient, a magnetic flux magnitude, a magnetic flux density, a capacitance value, a self-inductance value, a resonant frequency, a carrier wave frequency, a signal wave frequency, a modulation factor, a signal level, a noise level, and a temperature, for example.

Additionally, it is also conceivable that in a foreign matter detection system according to an embodiment of the present disclosure, multiple foreign matter detection techniques rather than just one of the foreign matter detection techniques discussed above may be combined and utilized jointly.

Although the foregoing embodiments are described only for the case of providing one transmitter coil and receiver coil each, an embodiment of the present disclosure is not limited to such a case, and may also be configured such that multiple (two or more) transmitter coils or receiver coils are provided, for example.

In addition, other LC resonators (resonant circuits) besides the LC resonator discussed earlier may be used in a contactless power supply system (for contactless power supply functionality or foreign matter detection functionality).

Also, although in the foregoing embodiments each coil (transmitter coil, receiver coil, detector coil) is taken to be spiral-shaped (planar) or helically wound in the direction of thickness, an embodiment of the present disclosure is not limited to such examples. For example, each coil may also have an alpha-winding shape in which a spiral-shaped coil folds back on itself in two layers, or spiral shapes with additional layers, for example.

The transmitter coil and receiver coil may also be configured with a coil whose shape enables reduced magnetic flux leakage, such as a FIG. 8 shape, a square grid shape, or a lattice shape.

The detector coil may also be integrated with a transmitter coil or a receiver coil, and a contactless power supply coil such as a transmitter coil or a receiver coil may be jointly used as a detector coil. Moreover, a coil used for purposes other than contactless power supply, such as an induction heating coil or a wireless communication coil may also be jointly used as a detector coil.

In other words, although the foregoing embodiments are described using the example of the case where a magnetic coupling element is taken to be a detector coil, it is also conceivable for the magnetic coupling element to be a coil such as a coil for contactless power supply (a transmitter coil or a receiver coil), an induction heating coil, or a wireless communication coil, such that these coils are also used for the purpose of detecting foreign matter.

Also, material such as magnetic material or metal material may also be provided in the transmitter of the power transmitting apparatus, in the receiver of the power receiving apparatus, and in the vicinity of the one or more detector coils, for the purpose of mitigating unwanted magnetic flux (magnetic field lines; magnetic field) leakage and improving transfer efficiency (power supply efficiency), for example.

Also, the respective resonant capacitors (particularly the resonant capacitor in the foreign matter detecting apparatus) are not limited to the case of using fixed capacitance values, and may also be configured with variable electrostatic capacitance values (such as a configuration that uses switches or other components to switch among connection pathways for multiple capacitive elements, for example). Configuring the resonant capacitors in this way makes it possible to control (optimize) the resonant frequency by adjusting the electrostatic capacitance values.

In addition, although the foregoing embodiments are described with reference to specific components of a power supply apparatus and an electronic device, for example, it is not necessary to provide all of the components, and furthermore, other components may be additionally provided. For example, it may also be configured such that a power supply apparatus (power transmitting apparatus) or an electronic apparatus (power receiving apparatus) is provided with communication functionality, some kind of detection functionality, control functionality, display functionality, functionality for authenticating a secondary device, functionality for determining that a secondary device is on top of a primary device, and functionality for detecting the presence of foreign matter according to a different technique than that according to an embodiment of the present disclosure, for example.

Also, although the foregoing embodiments are described by taking an example for the case of using load modulation for communication functionality, an embodiment of the present disclosure is not limited to such a case. For example, a modulation technique other than load modulation may also be used for communication functionality, or components such as a wireless communication antenna or wireless communication coil may be provided to communicate according to a technique other than modulation. Meanwhile, depending on the configuration of the contactless power supply functionality (the power transmitting apparatus and the power receiving apparatus) and the foreign matter detection functionality (the foreign matter detecting apparatus), it may also be configured such that communication functionality itself is not provided. Similarly, depending on the configuration of the contactless power supply functionality (the power transmitting apparatus and the power receiving apparatus) and the foreign matter detection functionality (the foreign matter detecting apparatus), it may also be configured such that portions of the various components (such as parts, units, and circuits) used in the description of the foregoing embodiments are not provided.

Also, although the foregoing embodiments are described by taking an example for the case where multiple (two) electronic devices are provided in a contactless power supply system, an embodiment of the present disclosure is not limited to such an example, and one electronic device, or three or more electronic devices, may also be provided in the contactless power supply system.

Furthermore, although the foregoing embodiments are described by taking a charging tray for portable electronic devices (CE devices) such as mobile phones as an example of a power supply apparatus, the power supply apparatus is not limited to such consumer charging trays, and is applicable as a charging device for various types of electronic devices. Moreover, it is not strictly necessary for the power supply apparatus to be a tray, and may also be a stand for an electronic device, such as a cradle, for example.

Also, although the foregoing embodiments are described by taking an electronic device as an example of a power recipient device, the power recipient device is not limited thereto, and may also be a power recipient device other than an electronic device (such as an electric car or other vehicle, for example).

Additionally, the present application may also be configured as below.

(1) A detecting apparatus including:

one or a plurality of magnetic coupling elements that include a plurality of coils;

a positioning unit disposed near at least one coil from among the plurality of coils included in the one or plurality of magnetic coupling elements; and a detector that measures an electrical parameter related to the one or plurality of magnetic coupling elements or to a circuit that at least includes the one or plurality of magnetic coupling elements, and determines from a change in the electrical parameter whether a foreign matter that generates heat due to magnetic flux is present.

(2) The detecting apparatus according to (1), wherein
the electrical parameter is a Q factor of the one or plurality of magnetic coupling elements or of a circuit that at least includes the one or plurality of magnetic coupling elements.

(3) The detecting apparatus according to (1) or (2), wherein
the positioning unit is disposed on an inner side of at least one coil from among the plurality of coils included in the one or plurality of magnetic coupling elements.

(4) The detecting apparatus according to any one of (1) to (3), further including:
a magnetic shielding material that reduces outward magnetic flux leakage, and is able to maintain a position relationship between the one or plurality of magnetic coupling elements and the positioning unit.

(5) The detecting apparatus according to any one of (1) to (4), wherein
at least a part of the positioning unit is a magnetic material.

(6) The detecting apparatus according to (4) or (5), further including:
a contactless power supply coil used for contactless power supply,
wherein the one or plurality of magnetic coupling elements and the contactless power supply coil are positioned on the magnetic shielding material by the positioning unit.

(7) The detecting apparatus according to (5) or (6), wherein
for a positioning unit made of a magnetic material and provided near at least two or more coils from among the plurality of coils included in the one or plurality of magnetic coupling elements, at least one from among a real part of permeability of the magnetic material in each positioning unit, an imaginary part of the permeability, outermost dimensions in X, Y, and Z directions, placement in the X, Y, and Z directions, and quantity of units to dispose are made to differ among the positioning units.

(8) The detecting apparatus according to any one of (5) to (7), wherein
in the magnetic material, a value of the real part of the permeability is greater than a value of the imaginary part of the permeability.

(9) The detecting apparatus according to any one of (5) to (8), wherein
an outermost dimension of a magnetic material of the positioning unit is smaller than outermost dimensions of at least one or more coils from among the plurality of coils included in the one or plurality of magnetic coupling elements.

(10) The detecting apparatus according to (9), wherein
the outermost dimension of the magnetic material of the positioning unit is smaller than innermost dimensions of at least one or more coils from among the plurality of coils included in the one or plurality of magnetic coupling elements.

(11) The detecting apparatus according to any one of (1) to (10), wherein
in the one or plurality of magnetic coupling elements, the plurality of coils are electrically connected such that magnetic flux produced from at least one or more of the plurality of coils and magnetic flux produced from remaining coils of the plurality of coils have approximately opposing orientations.

(12) The detecting apparatus according to (1), wherein
the plurality of coils included in the one or plurality of magnetic coupling elements are configured to be electrically connected by using a series connection, a parallel connection, or a combined series and parallel connection.

(13) The detecting apparatus according to any one of (1) to (12), wherein
the circuit that at least includes the one or plurality of magnetic coupling elements is a resonant circuit.

(14) A power receiving apparatus including:
one or a plurality of magnetic coupling elements that include a plurality of coils;
a positioning unit disposed near at least one coil from among the plurality of coils included in the one or plurality of magnetic coupling elements; and
a detector that measures an electrical parameter related to the one or plurality of magnetic coupling elements or to a circuit that at least includes the one or plurality of magnetic coupling elements, and determines from a change in the electrical parameter whether a foreign matter that generates heat due to magnetic flux is present.

(15) A power transmitting apparatus including:
a transmitter coil used for contactless power supply for a power recipient;
one or a plurality of magnetic coupling elements that include a plurality of coils;
a positioning unit disposed near at least one coil from among the plurality of coils included in the one or plurality of magnetic coupling elements; and
a detector that measures an electrical parameter related to the one or plurality of magnetic coupling elements or to a circuit that at least includes the one or plurality of magnetic coupling elements, and determines from a change in the electrical parameter whether a foreign matter that generates heat due to magnetic flux is present.

(16) A contactless power supply system including:
a power transmitting apparatus that wirelessly transmits power; and
a power receiving apparatus that receives power from the power transmitting apparatus,
wherein at least one of the power transmitting apparatus or the power receiving apparatus includes
a contactless power supply coil used for contactless power supply,
one or a plurality of magnetic coupling elements that include a plurality of coils,
a positioning unit disposed near at least one coil from among the plurality of coils included in the one or plurality of magnetic coupling elements, and
a detector that measures an electrical parameter related to the one or plurality of magnetic coupling elements or to a circuit that at least includes the one or plurality of magnetic coupling elements, and determines from a change in the electrical parameter whether a foreign matter that generates heat due to magnetic flux is present.

Note that the series of operations in the foregoing embodiments may be executed in hardware, and may also be executed in software. In the case of executing the series of operations in software, a program constituting such software may be executed by a computer built into special-purpose hardware, or alternatively, by a computer onto which programs for executing various functions are installed. For example, a program constituting the desired software may be installed and executed on a general-purpose personal computer.

Also, a recording medium storing program code of software that realizes the functionality of the foregoing embodiments may also be supplied to a system or apparatus. It is furthermore obvious that the functions are realized by a computer (or CPU or other control apparatus) in such a system or apparatus reading out and executing the program code stored in the recording medium.

The recording medium used to supply program code in this case may be a flexible disk, hard disk, optical disc, magneto-optical disc, CD-ROM, CD-R, magnetic tape, non-volatile memory card, or ROM, for example.

Also, the functions of the foregoing embodiment are realized by a computer executing read-out program code. In addition, some or all of the actual operations may be conducted on the basis of instructions from such program code by an OS or other software running on the computer. Cases where the functions of the foregoing embodiment are realized by such operations are also included.

Also, in this specification, the processing steps stating operations in a time series obviously encompass operations conducted in a time series following the described order, but also encompass operations executed in parallel or individually (for example, parallel processing or object-orientated processing), without strictly being processed in a time series.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

In other words, since the foregoing exemplary embodiments are ideal, specific examples of the present disclosure, various technically preferable limitations have been imposed thereon. However, the technical scope of the present disclosure it not to be limited to these embodiments, unless statements that particularly limit the present disclosure are made in their respective descriptions. For example, factors such as the types and quantities of materials used, processing times, processing sequences, and numerical conditions for respective parameters cited in the foregoing description are merely idealized examples. Furthermore, the dimensions, shapes, and positional relationships illustrated in the drawings used in the description are general and diagrammatic.

The invention is claimed as follows:

1. A detecting apparatus comprising:
   one or a plurality of magnetic coupling elements that include a plurality of coils;
   a positioning unit disposed near at least one coil from among the plurality of coils included in the one or plurality of magnetic coupling elements;
   a magnetic shielding material that reduces outward magnetic flux leakage, and is able to maintain a position relationship between the one or plurality of magnetic coupling elements and the positioning unit; and
   a detector that measures an electrical parameter related to the one or plurality of magnetic coupling elements or to a circuit that at least includes the one or plurality of magnetic coupling elements, and determines from a change in the electrical parameter whether a foreign matter that generates heat due to magnetic flux is present.

2. The detecting apparatus according to claim 1, wherein the electrical parameter is a Q factor of the one or plurality of magnetic coupling elements or of the circuit that at least includes the one or plurality of magnetic coupling elements.

3. The detecting apparatus according to claim 1, wherein the positioning unit is disposed on an inner side of at least one coil from among the plurality of coils included in the one or plurality of magnetic coupling elements.

4. The detecting apparatus according to claim 1, wherein at least a part of the positioning unit is a magnetic material.

5. The detecting apparatus according to claim 1, further comprising:
   a contactless power supply coil used for contactless power supply,
   wherein the one or plurality of magnetic coupling elements and the contactless power supply coil are positioned on the magnetic shielding material by the positioning unit.

6. The detecting apparatus according to claim 1, wherein, for the positioning unit made of a magnetic material and provided near at least two or more coils from among the plurality of coils included in the one or plurality of magnetic coupling elements, at least one of: a real part of permeability of the magnetic material in each positioning unit, an imaginary part of the permeability, outermost dimensions in X, Y, and Z directions, placement in the X, Y, and Z directions, and quantity of units to dispose are made to differ among the positioning units.

7. The detecting apparatus according to claim 6, wherein in the magnetic material, a value of the real part of the permeability is greater than a value of the imaginary part of the permeability.

8. The detecting apparatus according to claim 6, wherein an outermost dimension of the magnetic material of the positioning unit is smaller than outermost dimensions of at least one coils from among the plurality of coils included in the one or plurality of magnetic coupling elements.

9. The detecting apparatus according to claim 8, wherein the outermost dimension of the magnetic material of the positioning unit is smaller than innermost dimensions of at least one coils from among the plurality of coils included in the one or plurality of magnetic coupling elements.

10. The detecting apparatus according to claim 1, wherein in the one or plurality of magnetic coupling elements, the plurality of coils are electrically connected such that magnetic flux produced from at least one of the plurality of coils and magnetic flux produced from remaining coils of the plurality of coils have opposing orientations.

11. The detecting apparatus according to claim 1, wherein the plurality of coils included in the one or plurality of magnetic coupling elements are configured to be electrically connected by using a series connection, a parallel connection, or a combined series and parallel connection.

12. The detecting apparatus according to claim 1, wherein the circuit that at least includes the one or plurality of magnetic coupling elements is a resonant circuit.

13. A power receiving apparatus comprising:
   one or a plurality of magnetic coupling elements that include a plurality of coils;
   a positioning unit disposed near at least one coil from among the plurality of coils included in the one or plurality of magnetic coupling elements;
   a magnetic shielding material that reduces outward magnetic flux leakage, and is able to maintain a position relationship between the one or plurality of magnetic coupling elements and the positioning unit; and
   a detector that measures an electrical parameter related to the one or plurality of magnetic coupling elements or to a circuit that at least includes the one or plurality of magnetic coupling elements, and determines from a change in the electrical parameter whether a foreign matter that generates heat due to magnetic flux is present.

14. A power transmitting apparatus comprising:
a transmitter coil used for contactless power supply for a power recipient;
one or a plurality of magnetic coupling elements that include a plurality of coils;
a positioning unit disposed near at least one coil from among the plurality of coils included in the one or plurality of magnetic coupling elements;
a magnetic shielding material that reduces outward magnetic flux leakage, and is able to maintain a position relationship between the one or plurality of magnetic coupling elements and the positioning unit; and
a detector that measures an electrical parameter related to the one or plurality of magnetic coupling elements or to a circuit that at least includes the one or plurality of magnetic coupling elements, and determines from a change in the electrical parameter whether a foreign matter that generates heat due to magnetic flux is present.

15. A contactless power supply system comprising:
a power transmitting apparatus that wirelessly transmits power; and
a power receiving apparatus that receives power from the power transmitting apparatus,
wherein at least one of the power transmitting apparatus or the power receiving apparatus includes:
one or a plurality of magnetic coupling elements that include a plurality of coils,
a positioning unit disposed near at least one coil from among the plurality of coils included in the one or plurality of magnetic coupling elements,
a magnetic shielding material that reduces outward magnetic flux leakage, and is able to maintain a position relationship between the one or plurality of magnetic coupling elements and the positioning unit; and
a detector that measures an electrical parameter related to the one or plurality of magnetic coupling elements or to a circuit that at least includes the one or plurality of magnetic coupling elements, and determines from a change in the electrical parameter whether a foreign matter that generates heat due to magnetic flux is present.

\* \* \* \* \*